US012521482B2

(12) United States Patent
McNeer

(10) Patent No.: US 12,521,482 B2
(45) Date of Patent: Jan. 13, 2026

(54) MULTI-FLUID DELIVERY METHOD AND SYSTEM

(71) Applicant: Richard McNeer, Miami, FL (US)

(72) Inventor: Richard McNeer, Miami, FL (US)

(*) Notice: Subject to any disclaimer, the term of this patent is extended or adjusted under 35 U.S.C. 154(b) by 0 days.

(21) Appl. No.: 18/748,248

(22) Filed: Jun. 20, 2024

(65) Prior Publication Data

US 2025/0161561 A1 May 22, 2025

Related U.S. Application Data

(60) Provisional application No. 63/602,123, filed on Nov. 22, 2023.

(51) Int. Cl.
*A61M 5/14* (2006.01)
*A61M 5/142* (2006.01)
(Continued)

(52) U.S. Cl.
CPC ...... *A61M 5/1407* (2013.01); *A61M 5/14276* (2013.01); *A61M 5/16827* (2013.01);
(Continued)

(58) Field of Classification Search
CPC .. A61M 2005/1401; A61M 2202/0007; A61M 2202/0014; A61M 2202/0021; A61M 2202/04; A61M 2202/0464; A61M 2205/04; A61M 2205/33; A61M 2205/3327; A61M 2205/3379; A61M 2210/1003; A61M 5/14; A61M 5/1407; A61M 5/1408; A61M 5/1409; A61M 5/142; A61M 5/14244; A61M 5/14276; A61M 5/168; A61M 5/16804; A61M 5/16827; A61M 5/16877; A61M 5/16886; A61M 2025/0056; A61M 2039/0027; A61M 2039/0273; A61M 2039/0276; A61M 2039/0291; A61M 2202/048;
(Continued)

(56) References Cited

U.S. PATENT DOCUMENTS 8,246,602 B2 8/2012 Heruth et al.
10,159,838 B2 12/2018 Kim et al.
(Continued)

FOREIGN PATENT DOCUMENTS

WO 2020210634 A1 10/2020

*Primary Examiner* — Shefali D Patel

(57) ABSTRACT

Disclosed herein are methods and systems configured to distribute multiple fluids towards a target area. The target area may comprise a nerve ending within a patient's intrathecal space retaining cerebrospinal fluid (CSF). At least one fluid of the multiple fluids may be a therapeutic fluid comprising a medication. The distribution may be controlled to adjust a baricity of the therapeutic fluid with respect to the CSF, to provide more effective distribution towards the target area. An implementation may consider fluid densities, fluid flow rates, relative position and spatial orientation of the target area with respect to a point of fluid distribution to determine and control the fluid distribution toward the target area. An implementation may individually adjust fluid flow rates from multiple reservoirs to adjust therapeutic fluid baricity, dynamically modulate fluid extraction and aspiration through the intrathecal space using barbotage and respond to device or patient spatial orientation, permitting precise therapeutic fluid distribution prescriptions.

9 Claims, 20 Drawing Sheets

(51) Int. Cl.
*A61M 5/168* (2006.01)
*A61M 25/00* (2006.01)

(52) U.S. Cl.
CPC ... *A61M 25/007* (2013.01); *A61M 2202/0464* (2013.01); *A61M 2205/04* (2013.01); *A61M 2210/1003* (2013.01)

(58) Field of Classification Search
CPC .... A61M 25/00; A61M 25/007; A61M 31/00; A61M 39/0208; A61M 39/0247
See application file for complete search history.

(56) References Cited

U.S. PATENT DOCUMENTS

| | | | |
|---|---|---|---|
| 10,653,442 | B2 | 5/2020 | Anand et al. |
| 10,675,438 | B2 | 6/2020 | Anand et al. |
| 10,695,484 | B1 | 6/2020 | Radojicic |
| 11,013,900 | B2 | 5/2021 | Malek et al. |
| 11,224,348 | B2 | 1/2022 | Robinson et al. |
| 11,247,030 | B2 | 2/2022 | Browd et al. |
| 11,278,657 | B2 | 3/2022 | Depasqua et al. |
| 11,464,952 | B2 | 10/2022 | Badbada et al. |
| 11,744,939 | B2 | 9/2023 | Winek et al. |
| 2005/0020962 | A1 | 1/2005 | Reich et al. |
| 2019/0055578 | A1 | 2/2019 | Sah et al. |
| 2019/0160254 | A1 | 5/2019 | Anand et al. |
| 2020/0222628 | A1 | 7/2020 | John |
| 2021/0016000 | A1 | 1/2021 | Singh et al. |
| 2022/0096745 | A1 | 3/2022 | Riccardi et al. |
| 2022/0151656 | A1 | 5/2022 | Cameron |
| 2023/0321412 | A1 | 10/2023 | Tseng et al. |

MULTI-FLUID DELIVERY METHOD AND SYSTEM

CROSS-REFERENCE TO RELATED APPLICATIONS

This application claims the benefit of the earlier filing date of U.S. Provisional Patent Application No. 63/602,123 filed by Richard McNeer on Nov. 22, 2023, and the entire contents of the above-referenced application is incorporated by reference herein.

TECHNICAL FIELD

The present disclosure relates to the field of medicine delivery.

BACKGROUND

Some medications administered through an intrathecal catheter, such as baclofen and morphine, are isobaric (same density) relative to the cerebrospinal fluid (CSF) contained within the intrathecal cavity. Once administered, spread of the medication to therapeutic targets, for example, spinal nerves or nerve endings, relies on the relatively slow processes of diffusion and cerebrospinal fluid (CSF) circulation. Additionally, upon implantation, the relative position and distance between the intrathecal catheter tip and the therapeutic target may be highly variable.

Collectively, these factors have a negative impact on desired clinical efficacy as the medication concentration remains high near the catheter orifice and may not reach therapeutic concentrations at the desired target area. Attempts to overcome this limitation currently involve infusion of, at times, an ever-increasing volume of medication.

However, this leads to waste, premature depletion of medication reservoir volume and presence of therapeutic concentrations at structures that are not clinically relevant. In addition, although the volume of the medication may be increased, the desired therapeutic effect may not be fully realized as the increased medication may not reach the desired target area timely.

Hence, there is a need in the industry for a method and system for obtaining provided medication to a desired target area or region where the medications may be of different densities and further to increase the likelihood of the medication reaching the desired target area.

SUMMARY

Disclosed herein are methods and systems configured to distribute multiple fluids towards a target area. The target area may comprise a nerve ending within a patient's intrathecal space retaining cerebrospinal fluid (CSF). At least one fluid of the multiple fluids may be a therapeutic fluid comprising a medication. The distribution may be controlled to adjust the therapeutic fluid baricity with respect to CSF, to provide more effective distribution towards the target area. An implementation may consider fluid densities, fluid flow rates, relative position and spatial orientation of the target area with respect to the point of fluid distribution to determine and control the distribution toward the target area. An implementation may individually adjust fluid flow rates from multiple reservoirs to adjust therapeutic fluid baricity, dynamically modulate fluid extraction and aspiration through the intrathecal space using barbotage and respond to device or patient spatial orientation, permitting precise therapeutic fluid distribution prescriptions.

BRIEF DESCRIPTION OF THE DRAWINGS

The advantages, nature, and various additional features of the invention will appear more fully upon consideration of the illustrative embodiments described in detail in connection with the accompanying drawings, where like or similar reference numerals are used to identify like or similar elements throughout the drawings.

Figure 1:
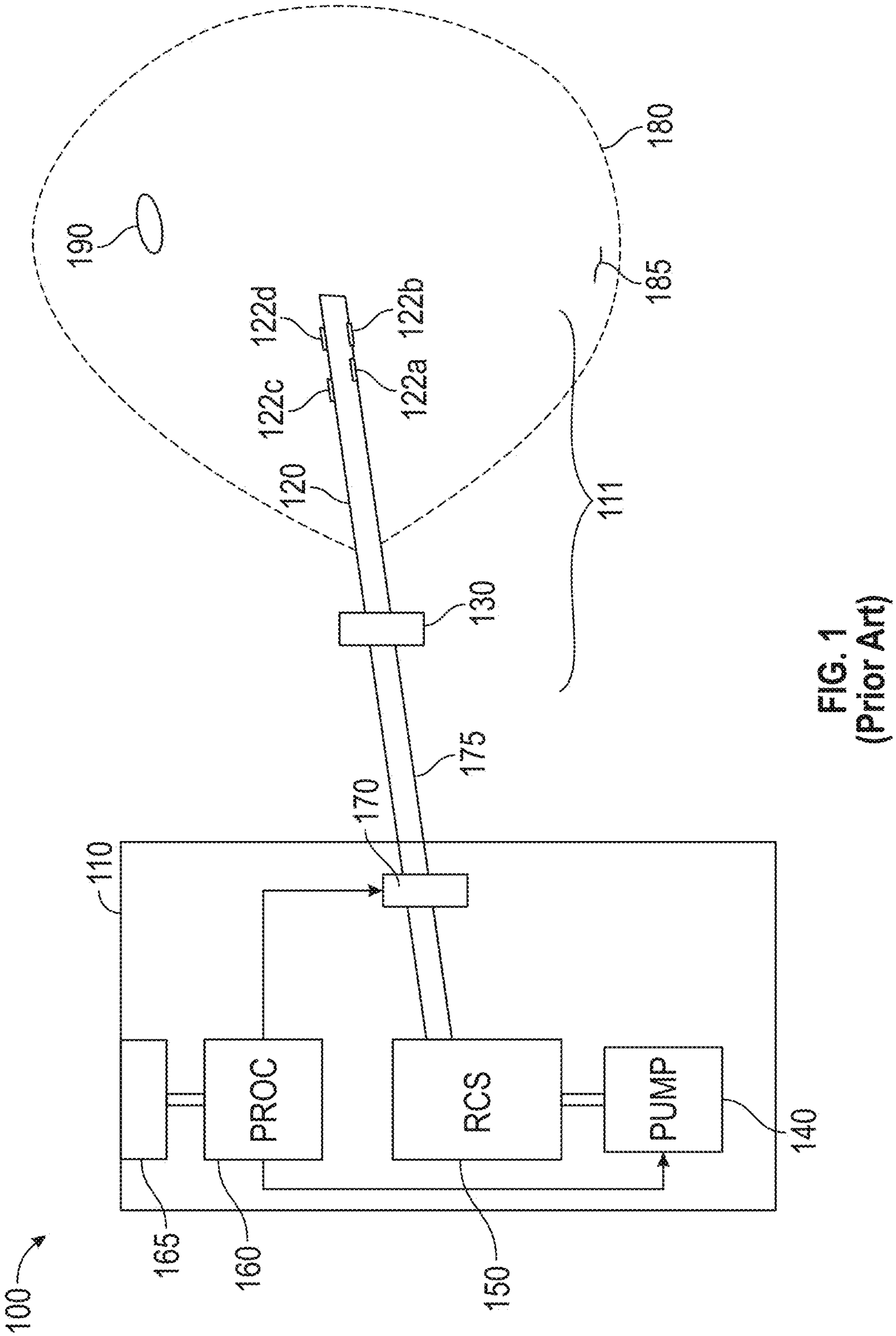
FIG. 1 (Prior Art)
FIG. 1 illustrates a block diagram of a conventional system for the delivery of one or more fluids to a cavity.

It is to be understood that the figures, which are not necessarily drawn to scale, and descriptions of the present invention described herein have been simplified to illustrate the elements that are relevant to one of ordinary skill for a clear understanding of the present invention. Elements not relevant for one of ordinary skill to understand the present invention may be omitted from the present disclosure. Because these omitted elements are well-known in the art, and because they do not facilitate a better understanding of the present invention, a discussion of such well-known elements is not provided herein.

Like reference symbols in the various drawings indicate like elements.

DETAILED DESCRIPTION

Note that the specific embodiments given in the drawings and following description do not limit the disclosure. On the contrary, they provide the foundation for one of ordinary skill to discern alternative forms, equivalents, and modifications that are contemplated by the inventor and encompassed in the claim scope.

Numerous alternative forms, equivalents, and modifications will become apparent to those skilled in the art once the above disclosure is fully appreciated. It is intended that the claims be interpreted to embrace all such alternative forms, equivalents, and modifications where applicable.

FIG. 1 illustrates a block diagram of a conventional system 100 including controller 110 and delivery system 111 for the delivery of one or more fluids, e.g., medications, to a target area 190. For example, medication, suitable for numbing or desensitizing an area including nerves/nerve ends, may be delivered through infusion port 130 to catheter (or a syringe or a lumen) 120, for the suppression of pain in a user. In another aspect anti-viral or anti-bacterial medication may be delivered through infusion port 130 to catheter 120 to an infected area.

Conventional medication delivery system 100 typically comprises a control or controlling unit or device 110, comprising pump 140, reservoir 150, containing a fluid (e.g., a numbing agent), and valve 170 in fluid communication with the reservoir 150. Further shown is processor 160 configured to control pump 140 and valve 170 to cause a flow of fluid from reservoir 150 to catheter 120. Processor 160 represents at least one general purpose processor, which when provided with appropriate instructions (i.e., code) becomes a special purpose processor configured to perform the tasks presented herein. Alternatively, processor 160 may comprise a special purpose processor (i.e., ASIC) or specially designed and dedicated hardware (i.e., electronic circuitry) that may be pre-programmed to control the release of fluid from reservoir 150 through the selective opening and closing of valve 170.

Processor 160, which when programmed, provides for the control of valve 170 and pump 140 to create a controlled flow of the fluid from reservoir 140 (i.e., a flowrate) through catheter 120, that is commensurate with a known or desired rate of distribution of the fluid within the designated area. The flowrate may be preprogrammed into processor 160 based on known or desired factors (e.g., medication, injection site, etc.). Alternatively, processor 160 may further comprise memory that may be altered by inputs entered through interface 165 that is configured to permit programming of operations to be performed by processor 160.

In the case of a pain suppression system, medications known in the art (e.g., opioid pain medication, anesthetics or Baclofen), may be delivered or pumped directly into a cavity (e.g., intrathecal cavity or the spinal column) 180 through catheter (or lumen) 120 inserted into cavity 180. The injected fluid may then be distributed or dispensed through one or more openings (outlets, orifices) 122*a*-122*d* situated at a distal end of catheter 120. As would be understood, the term "catheter" and "lumen" are used interchangeably herein. In one aspect of the discussion, herein, the term "catheter" may further comprise one or more catheters or lumens.

Transfer tubing 175 (i.e., extension catheter) may extend from valve 170 to infusion port 130 to allow for delivery of an appropriate fluid (e.g., medication) through the inserted catheter 120. In this illustrated example, infusion port 130 is shown as providing a means to enable fluid transferred through transfer tubing 175 to catheter 120. Port 130 may be, for example, a port-a-cath. Infusion ports are known in the art to provide a means of connecting or attaching different devices to an inserted element (e.g., a catheter) to provide for the administration of fluids (e.g., medications) to a patient or extract fluids from the patient. In one aspect of infusion ports, port 130 may include a screw thread or clip connection that enables the attachment of transfer tubes that include a matching screw thread or clip connection. In another aspect of infusion ports, port 130 may include a material suitable for the insertion of a needle, wherein the needle provides for a transfer of medication through tubing 175 to port 130.

The placement and positioning of catheter 120 within cavity 180, particularly with respect to target area 190 is of importance as it may determine the effectiveness and timeliness of applying a medication, for example, to target area 190. For example, in the case of cavity 180 being an intrathecal cavity containing a fluid (i.e., cerebrospinal fluid) therein, the location of catheter 120 with respect to target area 190 (e.g., a nerve ending) may determine whether an applied medication is timely applied to the nerve ending to alleviate a pain being experienced by a user or a patient.

In one aspect of the conventional system 100, the pump 140 and/or the reservoir 150 may be internal or external to a patient's body, such that reservoir 150 may be refilled to maintain the flow of a desired medication.

Figure 2:
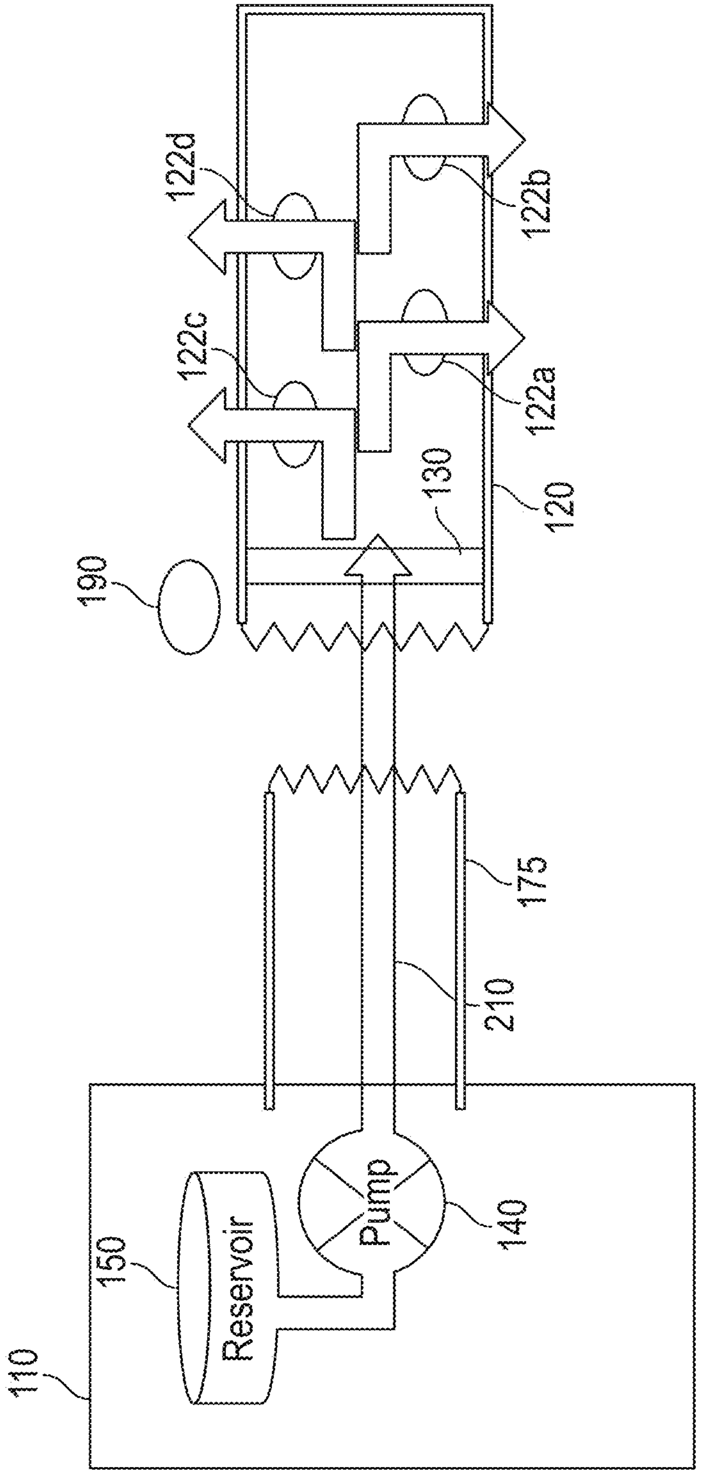
FIG. 2 (Prior Art)
FIG. 2 illustrates an exemplary delivery of a fluid when the delivery system is in a horizontal position.

FIG. 2 illustrates exemplary delivery of a fluid when the delivery system is in a horizontal position.

In this illustrated example, medication is transferred from reservoir 150, by a pressure applied by pump 140, to catheter 120 and expelled through one or more openings (outlets, orifices) 122*a*-122*d* in a distal end of catheter 120. Generally, the pressure or force provided to the flowing medication by pump 140 determines, in part, the extent the distributed medication extends from outlets (orifices) 122*a*-122*d*. Furthermore, the distribution is substantially equal through the illustrated outlets (orifices). The distribution may become more complex after fluid enters the surrounding fluid already present in the cavity.

However, as shown in this illustrated aspect, the distribution of a significant amount of the fluid dispensed from catheter 120 fails to be directed to a target area 190, as the position of the one or more catheter openings (outlets, orifices) 122*a*-122*d* is relatively distant from target area 190.

One improvement for greater distribution of fluid (or medication) to enable more of the fluid (or medication) to be directed toward target area 190 is to increase the flowrate (and thereby the amount) of medication dispensed from outlets (orifices) 122*a*-122*d* in the expectation that the increased medication will diffuse and achieve desired therapeutic concentrations at the target area 190. To provide for an increase in the delivery of medication to a target area 190, increased force or pressure exerted by pump 140 on the fluid (in conjunction with the size of the catheter openings (outlets, orifices) 122*a*-122*d*), may allow for a greater distribution of the medication toward the target area 190.

Figure 3A:
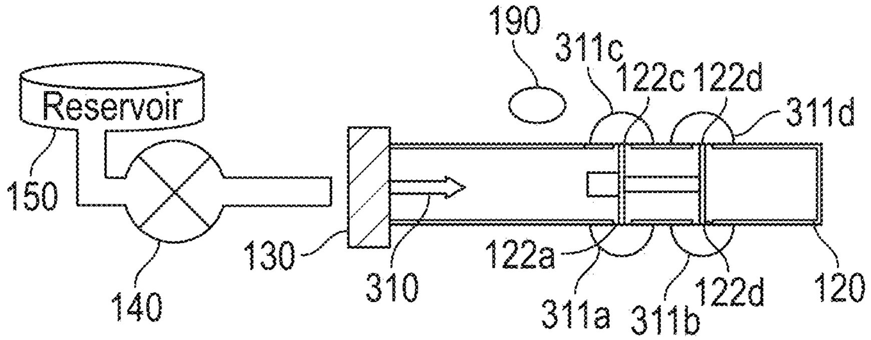
FIGS. 3A-3C illustrate an exemplary distribution of a fluid based on fluid flowrate.
Figure 3B:
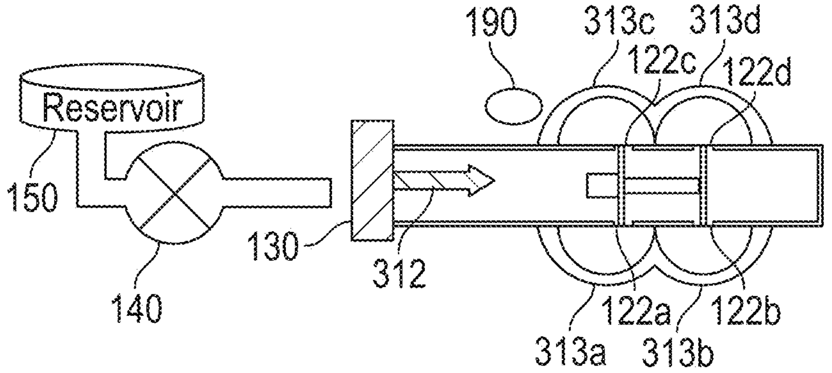
Figure 3C:
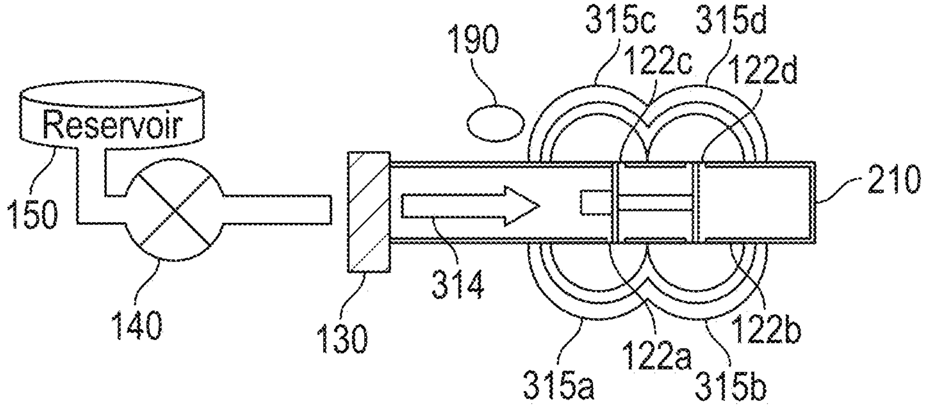

FIGS. 3A-3C illustrate examples of a distribution of a fluid (e.g., medication) based on flowrate, wherein the flowrate of fluid is increased to provide sufficient medication to a desired target area 190.

FIG. 3A illustrates a first flowrate 310 wherein the distribution of fluid 311*a*-311*d*, from corresponding ones of openings (outlets, orifices) 122*a*-122*d*, is shown. In this example, the distribution of the fluid is shown as being slightly distributed.

FIG. 3B illustrates a second flowrate 312 wherein a pressure exerted by the pump 140 is greater than pressure provided in FIG. 3A and, thus second flowrate 312, which is larger than the first flowrate 310, is achieved. In this case, the distribution of fluids 313*a*-313*d,* through corresponding ones of openings (outlets, orifices) 122*a*-122*d,* is shown as having increased.

FIG. 3C illustrates a third flowrate, wherein a pressure exerted by the pump 140 is greater that than of the pressure provided in FIG. 3B and, thus a third flowrate 314, larger than the second flowrate 312, is achieved. In this case, the distribution of fluids 315*a*-315*d,* through corresponding ones of openings (outlets, orifices) 122*a*-122*d,* is shown as having increased even further.

However, this approach (i.e., brute force) is not always successful, and may be inefficient. As shown in FIG. 3C, for example, the distribution of fluid (e.g., medication), while being closer to target area 190, fails to encompass target area 190. In addition, the increased distribution of fluid, by the increased pump pressure, leads to earlier depletion of fluid stored in reservoir 150. As therapeutic efficacy of a medication on (or in) the target area 190 and a distance of the medication from the target area 190 are inversely related, the efficacy of the medication in reaching target area 190 may not be sufficient to achieve a desired effect, even with a greater pressure exerted by pump 140.

In accordance with the principles of the invention, additional factors are introduced into the determination of applying fluids (e.g., medications) that provide for a more encompassing approach to the distribution of the fluids (e.g., medications) toward or within a target area 190.

Specifically, factors such as but not limited to the following examples are introduced:

- Baricity: a ratio of a density of a medication related to a density of the CSF within the intrathecal cavity;
- Barbotage: the repeated injection of fluid into a target area and the aspiration of a combination of the injected fluid and fluid within the intrathecal cavity;
- Delivery formulation; providing multiple fluids toward the target area within the intrathecal cavity, wherein a density of the provided fluid is selected to achieve a desired distribution; and
- Delivery orientation to provide more efficient and effective delivery of fluids (e.g., medication) to a desired target area based on an orientation of the target area within the intrathecal space or an orientation of the delivery device with respect to the target area within the body.

Controlling these additional factors provides for a unique and novel means for improving upon the distribution of one or more fluids toward a target area 190 within a cavity 180.

Figure 4A:
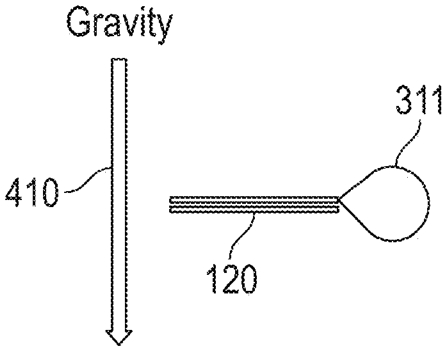
FIGS. 4A-4C illustrate exemplary consideration of baricity in the delivery of a fluid in accordance with the principles of the invention.
Figure 4B:
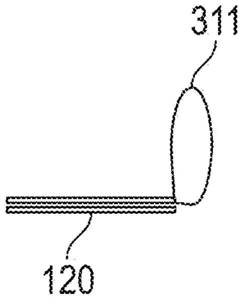
Figure 4C:
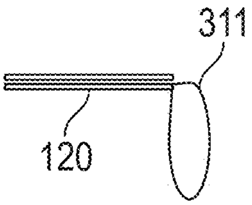

FIGS. 4A-4C illustrate exemplary consideration of baricity in the delivery of a solution of fluids in accordance with the principles of the invention.

FIG. 4A illustrates exemplary distribution 311 of a fluid at a tip or an orifice of a horizontally positioned catheter 120. In this illustrated example, the distributed fluid is one of an isobaric fluid, wherein the distributed fluid is of a substantially the same density as the density of a surrounding fluid (not shown). As shown, the direction of the distributed fluid remains substantially perpendicular to the gravity vector 410.

FIG. 4B illustrates a second exemplary distribution 311 of a fluid at tip or orifice from a horizontally positioned catheter 120. In this illustrated example, the distributed fluid is one of a hypobaric fluid, wherein the distributed fluid is of a lesser density than the density of a surrounding fluid within the cavity. As shown, the direction of the distributed fluid rises within the surrounding fluid (not shown) with respect to gravity vector 410 as the hypobaric fluid is lighter than the surrounding fluid. Hence, the hypobaric fluid travels in a direction opposite that of gravity vector 410.

FIG. 4C illustrates a third exemplary distribution 311 of a fluid at tip or orifice from a horizontally positioned catheter 120. In this illustrated example, the distributed fluid is one of a hyperbaric fluid, wherein the distributed fluid is of a greater density than the density of a surrounding fluid within the cavity. As shown, the direction of the distributed fluid descends within the surrounding fluid (not shown) with respect to gravity vector 410. Hence, the hyperbaric fluid travels in a direction in-line with that of gravity vector 410.

Figure 5A:
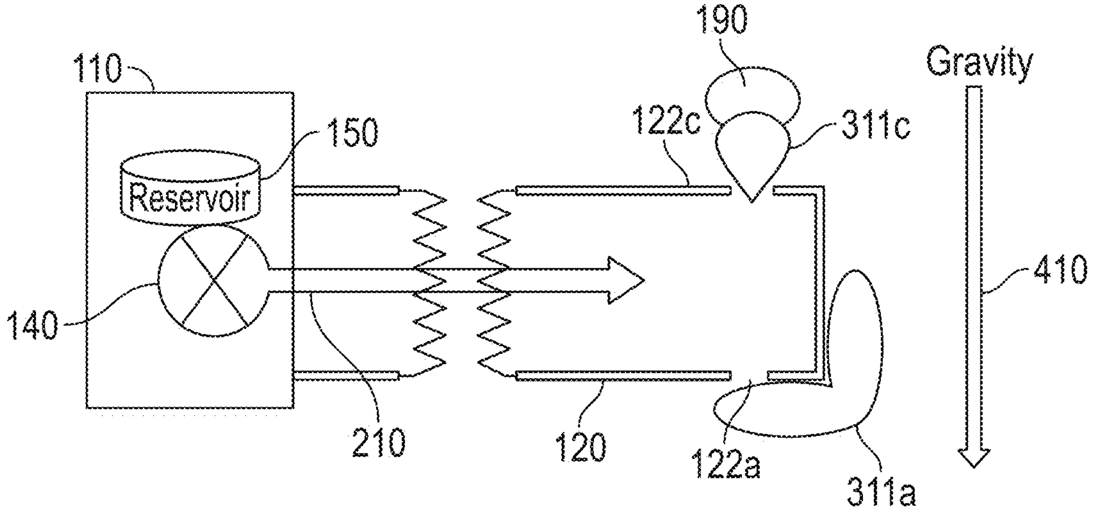
FIGS. 5A and 5B illustrate exemplary impact of baricity on the distribution of fluid from a horizontally positioned catheter.
Figure 5B:
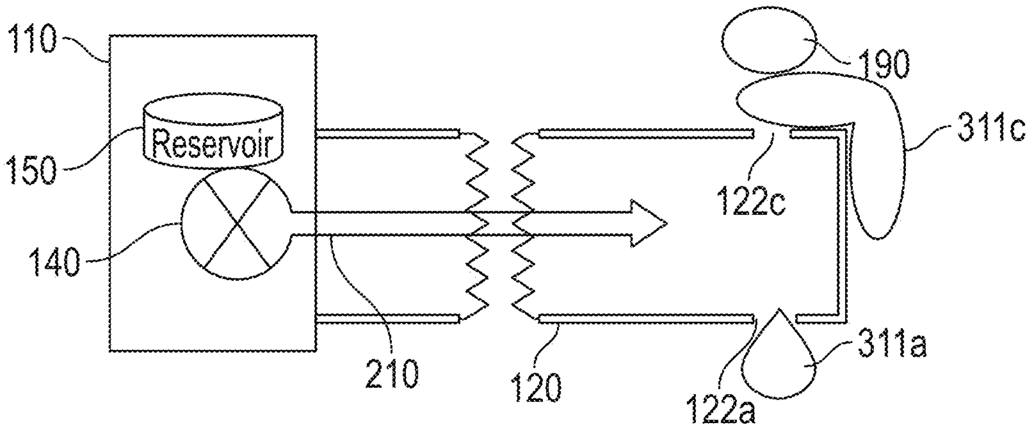

FIGS. 5A and 5B illustrate exemplary impact of baricity on the distribution of fluid from a horizontally positioned catheter.

FIG. 5A illustrates an example of a hypobaric fluid discharged from openings or orifices of a horizontally positioned catheter 120 using controlling unit or device 110 shown in FIG. 1. As shown, the discharged fluid moves upward (rising), with respect to gravity vector 410 as the density of discharged fluid is less than the density of the surrounding fluid. In this case fluids within distribution pattern 311*c* (corresponding to orifice 122*c*) are shown to rise toward target area 190. Similarly, fluids within distribution pattern 311*a* (corresponding to orifice 122*a*) are shown rising toward target area 190, as this fluid is of a lesser density than the surrounding fluid. The technical effect of adjusted baricity can be seen by contrast with the example given with reference to FIG. 3A wherein fluids having unadjusted baricity are shown extending downward as they encounter the surrounding fluid.

FIG. 5B illustrates an example of a hyperbaric fluid discharged from openings or orifices of horizontally positioned catheter 120, using controlling unit or device 110 shown in FIG. 1. As shown, the discharged fluid moves downward (descending), with respect to gravity vector 410, as the density of the discharged fluid is greater than that of the surrounding fluid. Accordingly, the discharged fluid moves downward and away from target area 190.

Figures 6A, 6B, 6C:
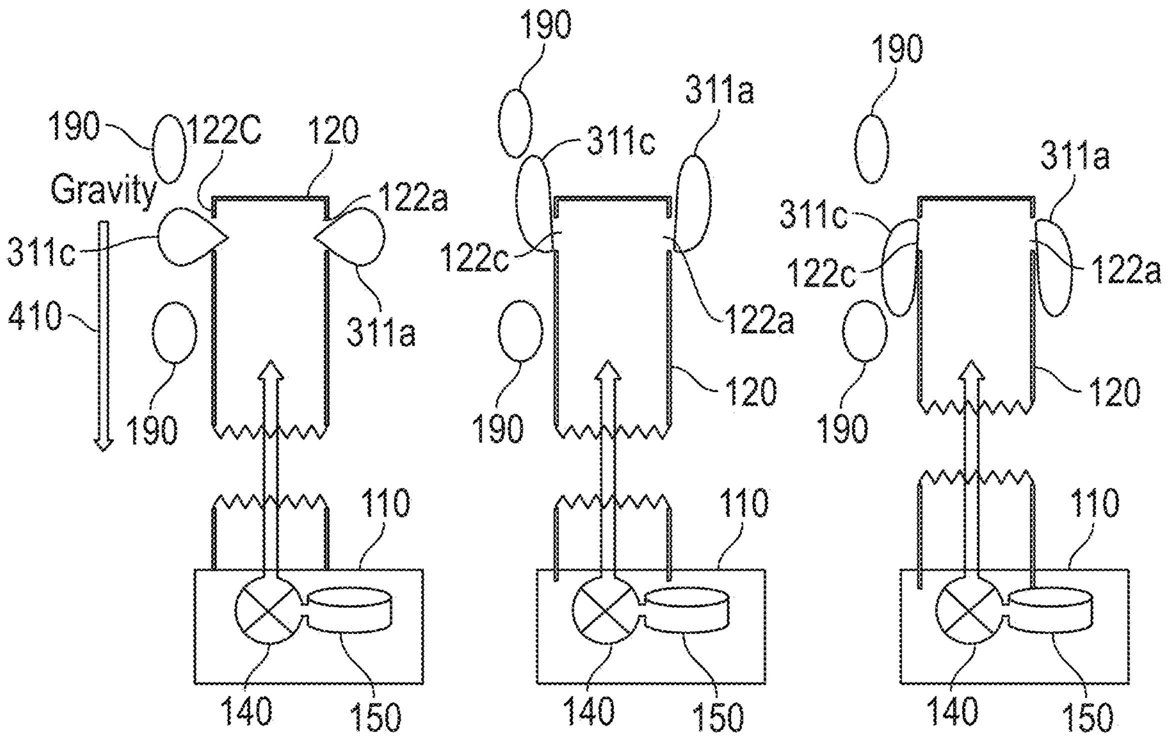
FIGS. 6A-6C illustrate exemplary impact of baricity on the distribution of fluid from a vertically positioned catheter.

FIGS. 6A-6C illustrate examples of the impact of baricity on the distribution of fluid from a vertically positioned catheter 120.

FIG. 6A illustrates an example of the distribution of an isobaric fluid from vertically positioned catheter 120 using controlling unit or device 110 shown in FIG. 1. In this illustrated case, the distributed isobaric fluid within distribution patterns 311*a,* 311*c,* being of a substantially same density as that of the surrounding fluid, remains substantially stable within the surrounding fluid. Hence, the use of an isobaric fluid fails to provide a desired effect of contacting target area 190.

FIG. 6B illustrates an example of the distribution of a hypobaric fluid from vertically positioned catheter 120 using controlling unit or device 110 shown in FIG. 1. In this illustrated case, the distributed hypobaric fluid within distribution patterns 311*a,* 311*c,* being of a lighter density than that of the surrounding fluid rises toward target area 190. Accordingly, the use of a hypobaric fluid, in this illustrated case, achieves a desired contacting effect on target area 190 when the target area 190 is above (i.e., gravitationally above) the location of catheter 120.

FIG. 6C illustrates an example of the distribution of a hyperbaric fluid from vertically positioned catheter 120 using the controlling unit or device 110 shown in FIG. 1. In this illustrated case, the distributed fluid within distribution patterns 311*a,* 311*c,* being of a higher density than that of the surrounding fluid falls or descends within the surrounding fluid. Accordingly, the use of a hyperbaric fluid, in this illustrated case, achieves a desired contacting effect on target area 190 when the target area 190 is below the location of catheter 120.

Thus, as shown, the positioning of outlets (orifices) with respect to target area 190, and the density of the discharged fluid provides additional factors that, as discussed and presented in accordance with the principles of the invention, may be utilized to improve the delivery toward a target area 190 of a fluid (e.g., a medication) and the effectiveness of the medication.

Figure 7A:
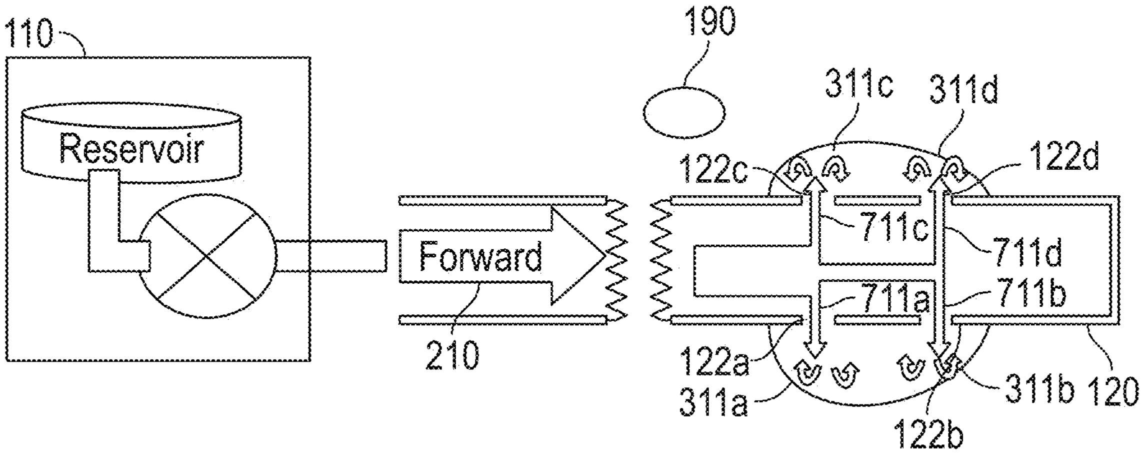
FIGS. 7A-7C illustrate exemplary impact of barbotage on the distribution of fluid from a horizontally positioned catheter.
Figure 7B:
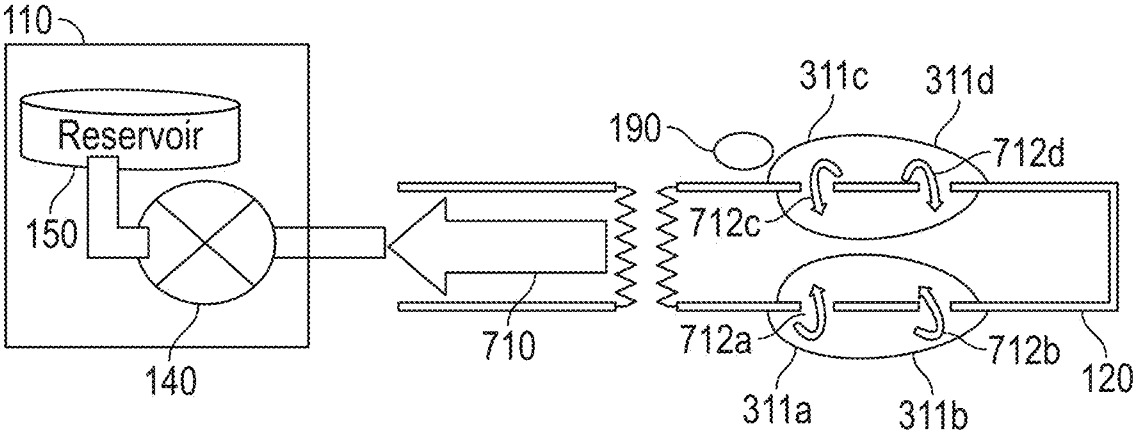
Figure 7C:
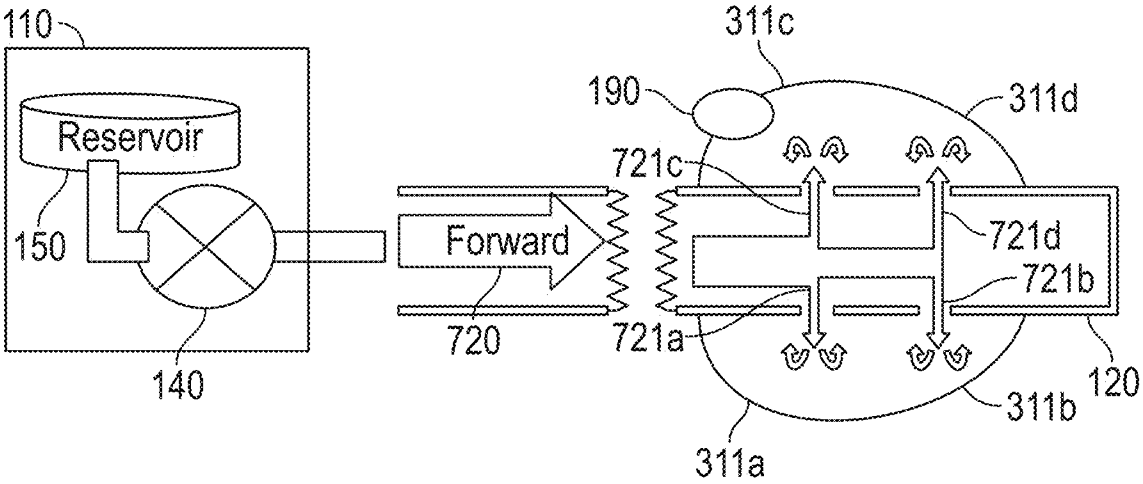

FIGS. 7A-7C illustrates exemplary impact of the process of barbotage on the distribution of fluid from a horizontally positioned catheter 120.

FIG. 7A illustrates an example of the injection (and distribution) of fluid through catheter 120 using system 100 shown in FIG. 1. In this illustrated example, forward flow of fluid 210 (see FIG. 2) through catheter 120 is shown, wherein fluid 711*a*-711*d* is distributed from corresponding ones of outlets (orifices) 122*a*-122*d* and achieves corresponding distribution patterns 311*a*-311*d*, respectively.

FIG. 7B illustrates an example of the extraction or aspiration of the distributed fluid within the area of distribution patterns 311*a*-311*d*, wherein the extracted fluid flows 712*a*-712*d*, are drawn from surrounding fluid (not shown) through corresponding outlets (orifices) 122*a*-122*d*. In the depicted implementation, the extracted fluid flows 712*a*-712*d* are a mixture of the originally injected fluid 210 (shown in FIG. 7A) and the surrounding fluid. The extracted fluid 710 is then provided to reservoir 150, wherein the extracted or aspirated fluid may be further mixed with the fluid within reservoir 150.

FIG. 7C illustrates an example of the re-injection of a combination of additional fluid 720 provided from reservoir 150 and the previously extracted fluid 710 (shown in FIG. 7B), wherein the distribution patterns 311*a*-311*d* associated with the re-injected fluids 720 is of a greater distribution. In this case, pump 140 is a bidirectional pump, which allows for the injection of fluids into, and the extract of fluids from, cavity 180 (depicted for example at least by FIG. 1). In the depicted implementation the combination of fluids 721*a*-721*b* is distributed from corresponding ones of the outlets (orifices) 122*a*-122*d*.

Barbotage, accordingly, provides improvement in the distribution of a fluid (e.g., a medication) toward target area 190.

In accordance with the principles set forth by the present disclosure, rates of fluid flow and timing of fluid flow may be determined as:

Net flowrate of an injected flow may be determined as:

$$\text{F\_net} = \text{net flow rate} \qquad (1)$$

$$\text{F\_net} \geq 0$$

Flowrate during injection phase of a barbotage cycle may be determined as:

$$\text{F\_inject} = \text{forward (injection) flow rate} \qquad (2)$$

$$\text{F\_inject} > \text{F\_net}$$

Flowrate during an 'extraction' phase of the barbotage cycle may be determined as:

$$\text{F\_extract} = \text{reverse (extraction) flow rate} \qquad (3)$$

$$\text{F\_extract} < 0$$

where a negative representation is chosen.

A length of time for an injection phase may be presented as:

$$\text{t\_inject} = \text{injection time} \qquad (4)$$

and a length of time for an extraction phase may be presented as:

$$\text{t\_extract} = \text{extraction time} \qquad (5)$$

The length of time (period) for one cycle of injection and extraction may be determined as:

$$\text{t\_period} = \text{t\_inject} + \text{t\_extract} \qquad (6)$$

A fluid injection to extraction (I:E) ratio may further be determined, as the relative amount of injection time to extraction time per barbotage cycle period. The I:E ratio may be used to specify/prescribe relative inspiratory and expiratory times during a cycle:

$$I:E\,\{\text{prescription parameters}\} \rightarrow I/E\{\text{ratio value}\}$$

Importantly, $$\text{t\_inject} = (I/(I+E))\,\text{t\_period} \qquad (7)$$

or $$\text{t\_inject} = ((I/E)/(I/E+1))\,\text{t\_period} \qquad (8)$$

and $$\text{t\_extract} = (E/(I+E))\,\text{t\_period} \qquad (9)$$

or $$\text{t\_extract} = (1/(I/E+1))\,\text{t\_period} \qquad (10)$$

From the above referred to analysis, the following derivations may be made.

Given, $$\text{F\_net} = (\text{F\_inject t\_inject} + \text{F\_extract t\_extract})/\text{t\_period} \qquad (11)$$

Then, $$\text{F\_net t\_period} = \text{F\_inject t\_inject} + \text{F\_extract t\_extract} \qquad (12)$$

$$\text{F\_extract t\_extract} = \text{F\_net t\_period} - \text{F\_inject t\_inject}$$

$$\text{F\_extract} = (\text{F\_net t\_period} - \text{F\_inject t\_inject})/\text{t\_extract}$$

-continued $$F\_extract = (F\_net\ t\_period - ((I/E)/(I/E+1))\ F\_inject\ t\_period)/((1/(I/E+1))\ t\_period)$$

$$F\_extract = ((I/E+1)\ F\_net\ t\_period - (I/E)\ F\_inject\ t\_period)/t\_period$$

$$F\_extract = (I/E+1)\ F\_net - (I/E)\ F\_inject$$

Thus, the rate of fluid extraction, F_extract, may be calculated as a function of I:E ratio, net rate (F_net) and injection rate (F_inject).

As an example of the utilization of barbotage in the improved distribution of one or more fluids (e.g., medication), a fluid injection/fluid extraction (I:E) ratio may be determined from Equation 12 as:

let F_net equal 2 ml/min; and
F_inject equal 5 ml/mm,
then
F_extract may be determined as −1 ml/mm.

Table 1 illustrates representative values of F_extract calculated as a function of I:E ratio, net rate (F_net) and the injection rate (F_inject). In Table 1, I:E default is 1:1, and flow rate values are in ml/min. Combinations of F_net and F_inject that give values of F_extract greater than or equal to 0 are not shown in Table 1.

TABLE 1

F_extract (ml/min) as a function of F_net and F_inject.

| F_net | F_inject (ml/min) | | | | |
|---|---|---|---|---|---|
| (ml/min) | 1 | 3 | 5 | 7 | 9 |
| 0 | −1 | −3 | −5 | −7 | −9 |
| 1 | | −1 | −3 | −5 | −7 |
| 2 | | | −1 | −3 | −5 |
| 3 | | | | −1 | −3 |
| 4 | | | | | −1 |

Default I:E is 1:1

Determining a prescription for given F_net and F_inject such that F_extract is closer in absolute value to F_inject may be desirable. To accomplish this, an appropriate I:E ratio with less time given to fluid extraction relative to fluid injection is required to be calculated. In one aspect of the invention, a timing of the injection of one or more fluids to the extraction of the fluids may be further determined as:

Given F_net, F_inject and F_extract, an injection/extraction ratio (I/E) may be determined as:

$$F\_extract = (I/E+1)\ F\_net - (I/E)\ F\_inject \tag{13}$$

Then, $$F\_extract = (I/E)\ F\_net + F\_net - (I/E)\ F\_inject \tag{14}$$

$$F\_extract = (E/E)(F\_net - F\_inject) + F\_net \tag{15}$$

$$(I/E)(F\_net - F\_inject) = F\_extract - F\_net \tag{16}$$

and, an Injection/Extraction ratio may be determined as:

$$I/E = (F\_net - F\_extract)/(F\_inject - F\_net) \tag{17}$$

Examples of I:E ratios needed to allow selected values of F_extract are shown in Table 2.

TABLE 2

I:E ratio as a function of F_extract for fixed F_net and F_inject

| | I:E ratio | |
|---|---|---|
| F_extract | Value | Prescription |
| −1 | 1.00 | 1:1 |
| −2 | 1.33 | 1:0.75 |
| −3 | 1.67 | 2:1.2 |
| −4 | 2.00 | 2:1 |
| −5 | 2.33 | 2:0.86 |
| −6 | 2.67 | 3:1.13 |
| −7 | 3.00 | 3:1 |
| −8 | 3.33 | 3:0.9 |
| −9 | 3.67 | 4:1.09 |
| −10 | 4.00 | 4:1 |

F_net = 2 ml/min, F_inject = 5 ml/min

Using as an example the previously referred to condition wherein F_extract is closer in value to F_inject, and specifying F_net=2 ml/min, and F_inject=5 ml/min, then a required I:E may be determined from Table 2 as 2.33.

From a determination of the I/E ratio (e.g., 2.33), fluid timing associated with the fluid inject phase and the fluid extract phase may be determined as:

F_inject/F_extract (I/E)=2.33
F_inject=2.33 F_extract
Let F_inject=2
Then
F_extract=0.86
Accordingly, the F_inject time is:
2:0.86.

That is, in the case of administering a solution into the intrathecal cavity, time for the injection of the medication (i.e., 5 ml/min) into the intrathecal cavity is slightly greater than two (2) times the time for the extraction of the fluid (i.e., 5 ml/min) from the cavity.

In an illustrative example, changing I:E ratio changes t_inject and t_extract as expected. Additionally, the volumes injected and extracted also necessarily change. However, F_net remains constant. A prescription strategy that uses injected and extracted volumes (instead of flows) may be implemented. However, this strategy may not be intuitive. In some cases, selecting large values of t_period may be counterproductive.

Hence, in accordance with the principles of the invention, processor 160 may provide instructions to pump 140 to control an injection flow of fluids into port 130 for a first known period of time and an extraction, or aspiration, flow of fluids from port 130, for a second known period of time, wherein the first and second known periods of time satisfy the determined I:E ratio.

Accordingly, the aspirated (or extracted) fluid comprises a mixture of distributed fluid and fluid that is known to exist in (or contained within) the space (cavity), to utilize the process of barbotage to provide an additional factor that, in accordance with the principles of the invention, provides for the improvement in the delivery and the effectiveness of a fluid (e.g., a medication) toward target area 190. In one aspect of the invention, the aspirated mixture of distributed and contained fluid may be provided to one or more of the illustrated reservoirs, wherein a further mixture of fluid within a corresponding reservoir and the aspirated fluid may be re-injected into the space.

FIGS. 8A-8D illustrate exemplary delivery systems for the distribution of multiple fluids in accordance with the principles of the invention.

Figure 8A:
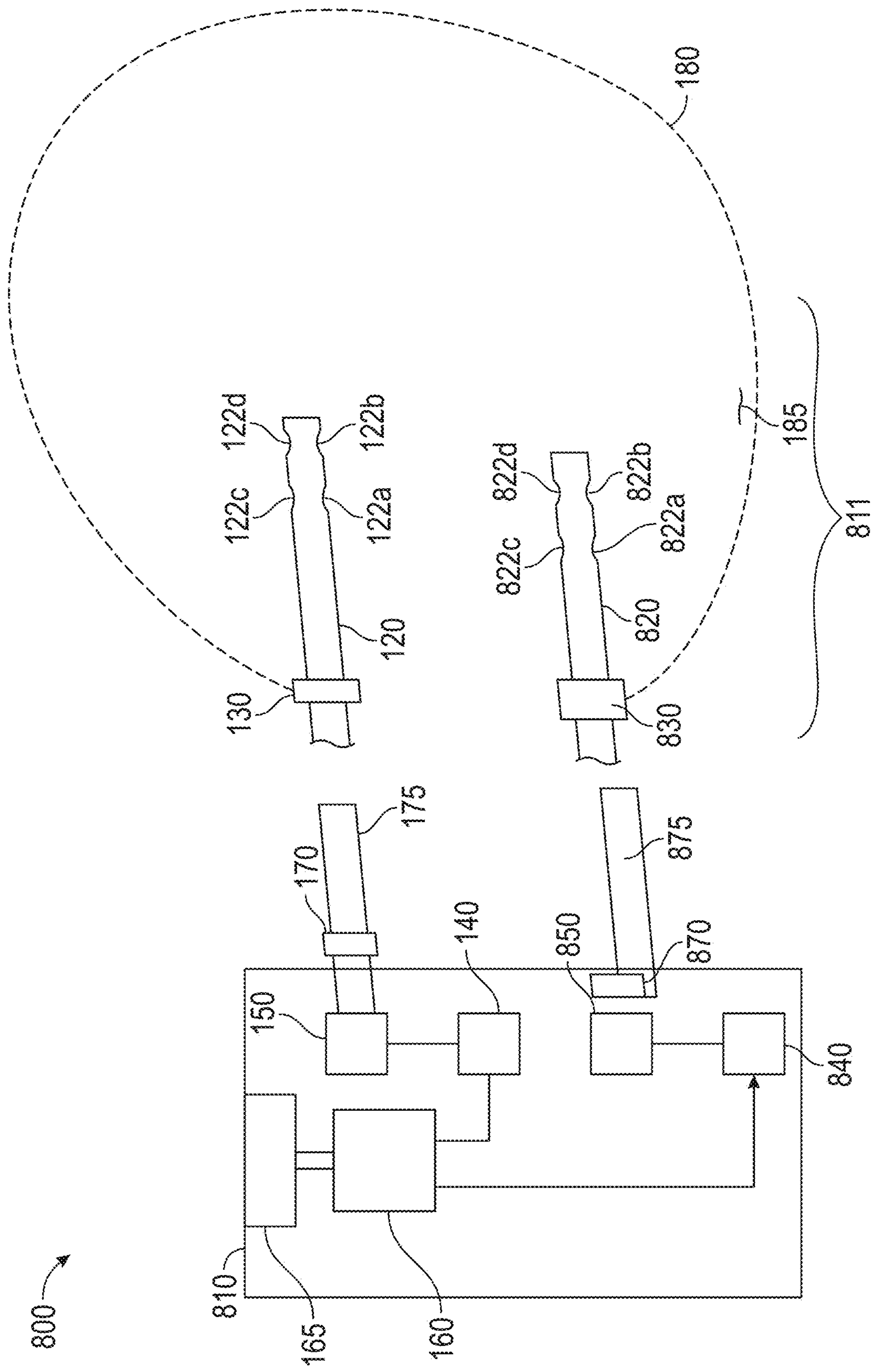
FIGS. 8A-8D illustrate exemplary delivery systems for the distribution of multiple fluids in accordance with the principles of the invention.

FIG. 8A illustrates a first exemplary embodiment of a system for the control, management and distribution of a plurality of fluids into a cavity to achieve a desired effect in accordance with the principles of the invention.

In this illustrated first exemplary embodiment system 800 comprises control device 810 and delivery system 811. In the depicted implementation the delivery system 811 comprises infusion port 830 and a plurality of catheter elements 120 inserted within cavity 180.

In the depicted implementation control device 810 is similar to control device 110, shown in FIG. 1, wherein control device 810 is depicted in FIG. 8A comprises processor 160, pump 140, reservoir 150 and valve 170. Control device 810 further includes a second pump 840, second reservoir 850 and second valve 870, wherein the second pump 840 and second reservoir 850 operate, under the control of processor 160, independently of, and in conjunction with, pump 140 and reservoir 150, as will be discussed.

Further illustrated are infusion port 130 (and catheter 120) fluidly communicating with valve 170 through transfer tube 175, as previously discussed, and second catheter 820 in fluid communication with second reservoir 850 through second infusion port 830 and second valve 870. Further illustrated is transfer tube 875 that supplies fluid from valve 870 to catheter 820.

In accordance with this aspect of the invention, the operation of pump 140 and second pump 840 may be programmed in processor 160 though interface 165 (e.g., Graphic User Interface (GUI)) to establish flowrates of the fluids contained within each of reservoir 150 and second reservoir 850. In one aspect of the invention, interface 165 may provide a presentation of the flow rates, wherein flow rates may be computed by processor 160 based on one or more preset conditions. In one aspect of the invention, pump 140 (and a corresponding fluid flowrate) and second pump 840 (and a corresponding fluid flowrate) may be independently controlled to provide a solution (i.e., a mixture of fluids from reservoirs 150, 850), wherein the characteristics of solution formed by the fluids from reservoirs 150, 850 may be adjusted to achieve desired effects based on one or more of baricity, barbotage, orientation and delivery. In this illustrated example, the solution is formed within cavity 180, as the fluids are independently provided to cavity 180.

For example, when the density of each of the fluids within reservoir 150 and second reservoir 850 are substantially equal and an isobaric solution is desired, then flowrates through each catheter 120 and 820 may be commensurate. Alternatively, when the densities of the fluids within reservoir 150 and second reservoir 850 are different, then the quantity of the fluids, based on a flowrate from corresponding reservoirs 150, 850, may be independently adjusted to create a substantially isobaric solution, a hypobaric solution or a hyperbaric solution. In an example, when a hypobaric solution is desired and the density of the fluid within second reservoir 850 is less than that of the fluid in the reservoir 150, then the flowrate of the fluid from second reservoir 850 may be greater than the fluid within reservoir 150 to create and distribute a solution (i.e., combination of more than one fluid) that when mixed at the point of distribution is hypobaric. In another example, when a hyperbaric solution is desired and the density of the fluid within second reservoir 850 is greater than that of the fluid in the reservoir 150, then the flowrate of the fluid from second reservoir 850 may be greater than the fluid within reservoir 150 to create and distribute a solution that when mixed at the point of distribution is hyperbaric.

In one aspect of the invention, the flowrates from the one or more reservoirs may be determined to achieve a desired baricity through a determination of an amount and the densities, of each of the fluids provided to the cavity by reservoirs 150, 850 during a known period of time.

Accordingly, a density of the solution form from the mixture of the fluids within reservoirs 150, 850 may be determined as:

$$D_S = ((D_1 \times V_1 + D_2 \times V_2)) / (V_1 + V_2) \qquad (18)$$

Wherein $D_S$ is the density of the solution, $D_1$, $D_2$ are the density of the fluids 1, 2

$V_1$, $V_2$ are the volumes of the fluids 1, 2.

The baricity of the solution with regard to the fluid within the cavity (e.g., CSF) may then be determined from the determined density of the solution.

Figure 8B:
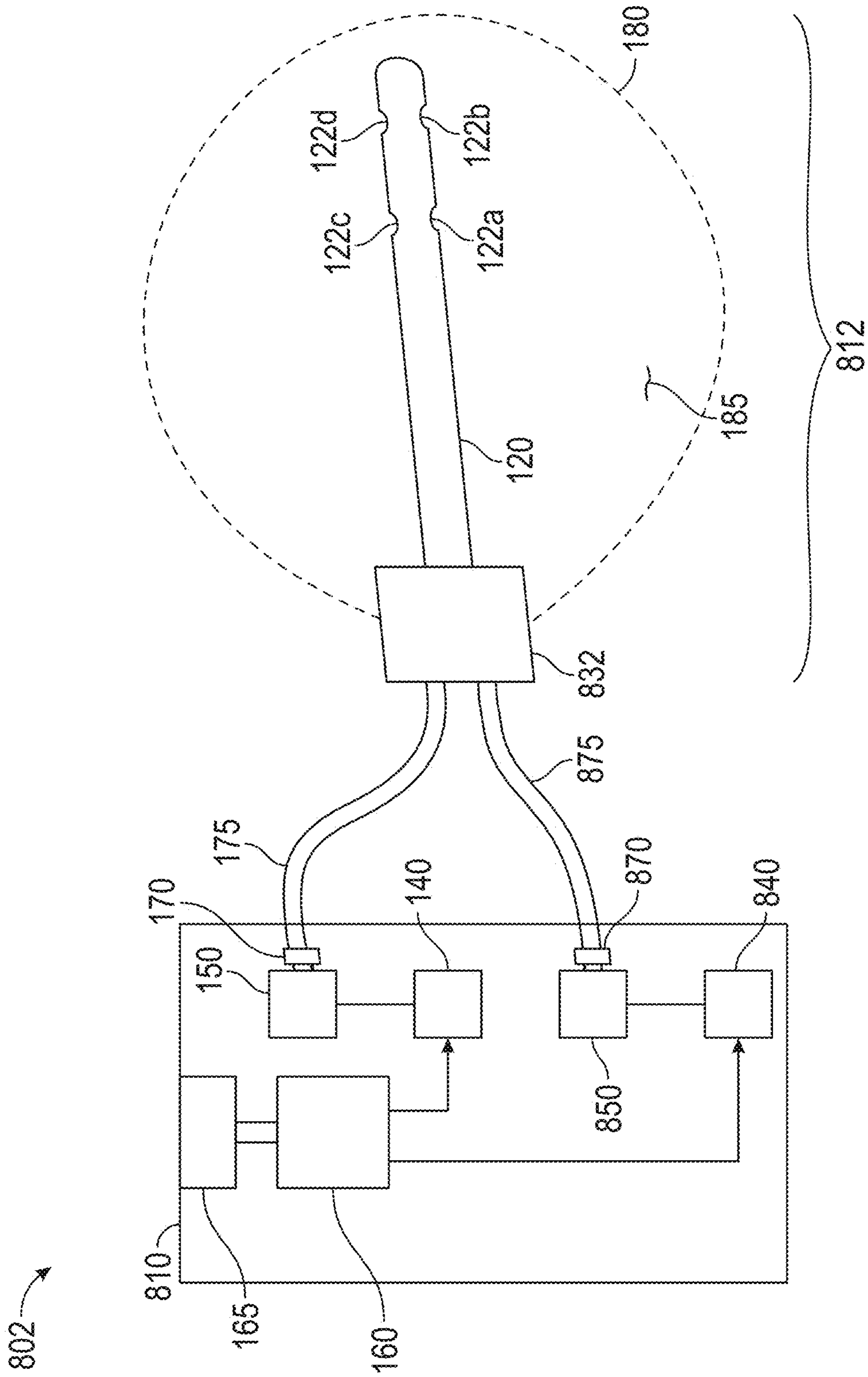

FIG. 8B illustrates a second exemplary embodiment of a system for the control, management and distribution of a plurality of fluids into a cavity or space to achieve a desired effect in accordance with the principles of the invention.

System 802, similar to system 800 shown in FIG. 8A, comprises control device 810 and delivery system 812 comprising infusion port 832 and catheter 120 inserted within cavity 180.

In this illustrated second exemplary embodiment, fluid drawn from reservoir 150 and fluid drawn from second reservoir 850 enter infusion port 832, wherein a solution, formed by the two fluids, may be distributed through one or more of the illustrated orifices 122*a*-122*d*, as previously discussed. In this illustrated second embodiment, the mixture of the plurality of fluids received by port 832 is formed within catheter 120 for subsequent distribution into cavity 180.

As previously discussed, characteristics of a desired distributed solution may be achieved by an appropriate selection of flowrate from reservoir 150 and second reservoir 850. Appropriate selection of flowrate may be determined with regard to one or more of baricity, barbotage, orientation and delivery by determining a required volume of each of the fluids.

Figure 8C:
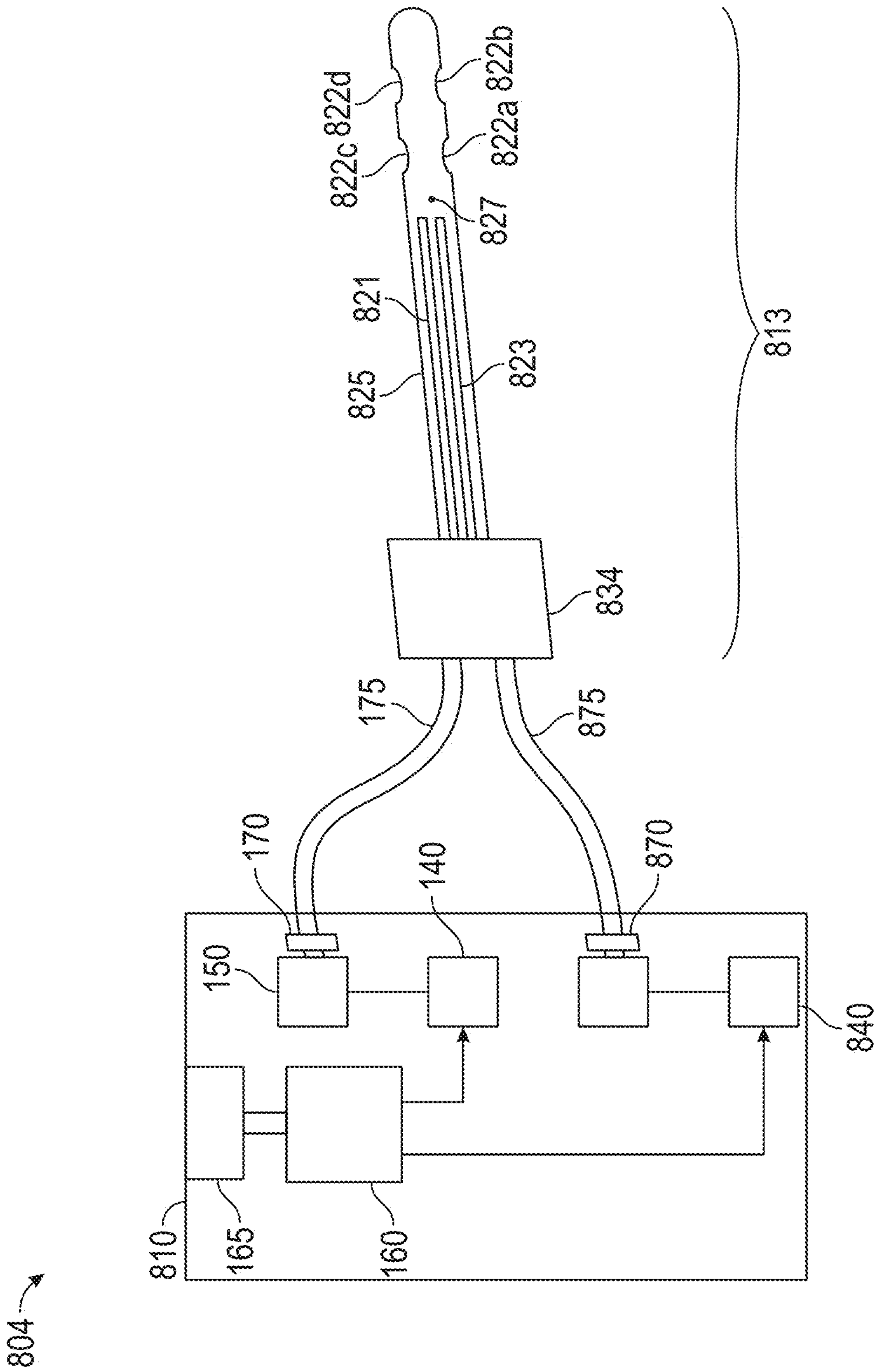

FIG. 8C illustrates a third exemplary embodiment of a system for the control, management and distribution of a plurality of fluids into a cavity to achieve a desired effect in accordance with the principles of the invention.

Similar to the system shown in FIGS. 8A and 8B, third exemplary system 804 depicted by FIG. 8C comprises control device 810 and delivery system 813 comprising infusion port 834 and catheters 821, 823 contained within sheathing 825, which is inserted within cavity 180 (not shown). Sheathing element 825, similar to catheter 820, shown in FIG. 8A, comprises at least one opening (outlet, orifice) 822*a*-822*d*, from which fluid entering sheathing 825 may be dispensed.

In accordance with this aspect of the invention, fluid from reservoir 150 and second reservoir 850 may be transferred through infusion port 834 and presented to corresponding ones of catheter 821, 823. Fluids exiting catheters 821, 823 may subsequently enter mixing area 827 within sheathing 825. In this case, a solution having the desired characteristics may be formed prior to dispensing through openings 822*a*-822*d*. As discussed previously, the characteristics of the solution formed in mixing area 827 may be specified or determined to allow for the rapid distribution of the solution through a fluid (e.g., CSF) within cavity 180.

Figure 8D:
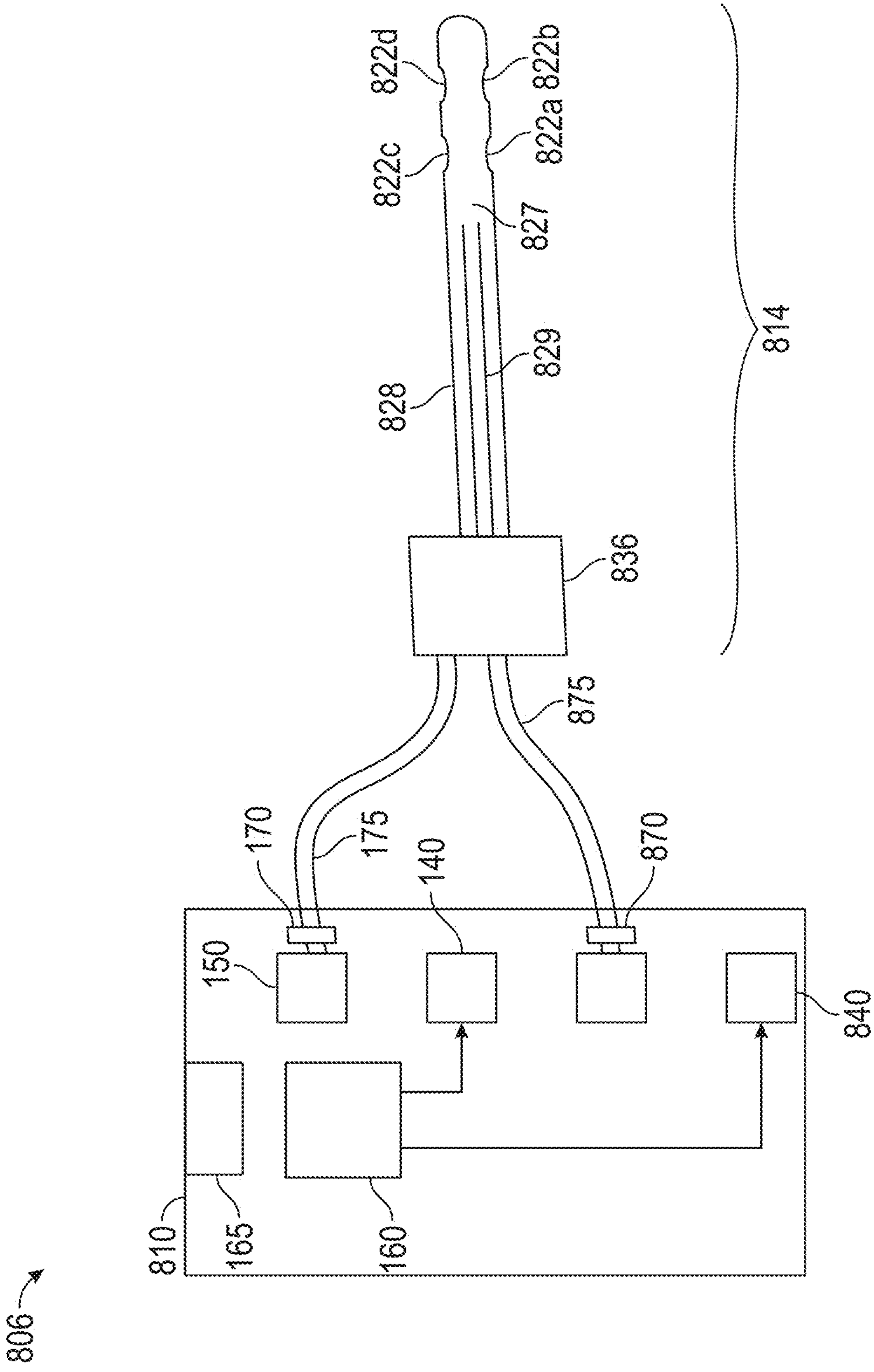

FIG. 8D illustrates a fourth exemplary embodiment of a system for the control, management and distribution of a plurality of fluids into a cavity to achieve a desired effect.

Similar to the system shown in FIGS. 8A-8C, fourth exemplary system 806 comprises control device 810 and delivery system 814. In the depicted implementation, the delivery system 814 comprises catheters 828, 829, wherein catheter 829 is positioned substantially concentrically within catheter 828. In the depicted implementation, catheter 828 is inserted within a cavity 180 (not shown, depicted at least by FIG. 1).

In accordance with the principles of this embodiment of the invention, catheter 828 provides a first fluid (e.g., medication) from a corresponding one of the illustrated reservoirs to mixing area 827. In the depicted implementation, catheter 828 provides a second fluid (e.g., saline) from a corresponding one of the illustrated reservoirs to mixing area 827, wherein desired characteristics of the solution formed by the mixture of the first and second fluids may be determined as discussed and distributed through the illustrated at least one opening (outlet, orifice) 822*a*-822*d*.

Although the above discussion refers to catheters 120, 820, 821, 823, 825, 828, 829 as including at least one openings or orifices located on an outer surface of the illustrated catheter, it would be recognized by those skilled in the art that the illustrated catheters may include the use of a syringe (i.e., a needle comprising a single opening at a distal end) to provide for the transfer of fluids from the illustrated reservoirs (150, 850) without altering the scope or operation of the invention claimed. The illustrated infusion ports may be integral to, or remove from, the illustrated catheters and/or syringe.

In addition, although the present invention is discussed with regard to the illustrated horizontal positioning of the illustrated catheters (FIGS. 8A-8D), it would be recognized by those skilled in the art, that the systems discussed, herein, are also applicable to a vertical orientation of the illustrated catheters or of a patient in a manner similar to that shown in FIGS. 6A-6C.

In an example of the administration of a medication, such as morphine, for example, into the intrathecal cavity a solution using a combination of morphine, which is known to be isobaric, with respect to the CSF fluid within the intrathecal cavity (approximately 1.0068 g/ml), and a saline solution (density approximately 1.046 g/ml) may, in accordance with the principles of the invention, be formed create a solution that may be one of hypobaric or hyperbaric that allows the solution created to travel within the CSF to target area 190 more quickly than that of an application of morphine alone.

In one aspect of the invention, to achieve a solution of a desired hypobaric baricity (with respect to the CSF and to a location of the target area within the CSF), a flowrate associated with a saline solution may be selected to be twice that of a flowrate associated with the morphine medication to create the desired hypobaric solution. As shown, the hypobaric solution rises within the surrounding CSF to arrive at a target area 190 in a more directed manner.

Alternatively, a solution of morphine and dextrose solution (density approximately 1.544 g/ml) may be formed, to create a hyperbaric solution, to control the flow of the combined solution downward toward a desired target area 190. In this case, a flowrate of the dextrose solution may be equal to that of the flowrate of the morphine solution to formulate a mixture having a greater density than that of the surrounding CSF.

In accordance with the principles of the invention, the effectiveness and efficiency of a solution applied to target area 190 may be substantially increased when factors such as baricity, barbotage and orientation are considered and adjusted in providing a medication to a target area 190.

Although morphine is discussed, it would be recognized by those skilled in the art, that other medications (e.g., Tetracaine, Novocain, etc.) may be utilized in preparing a solution for the administration of the delivery of a solution that is formulated to travel more quickly toward a desired target area.

Furthermore, it would be understood and recognized by those skilled in the art that other combinations of flowrates between a first fluid and a second fluid (one of which may be a medication) may be selected to achieve a desired effect. For example, when target area 190 is positioned laterally with respect to an insertion point of catheter 120, a first fluid (e.g., morphine) flowrate may be greater than that of a second fluid flowrate (e.g., saline) to create a solution having a baricity slightly greater than the baricity of the CSF, wherein the resultant solution (or medication) moves slowly through the CSF to provide a longer-term effect on target area 190.

FIGS. 9A-9D illustrate front views of exemplary embodiments of the entry ports associated with the systems shown in FIGS. 8A-8D.

Figure 9A:
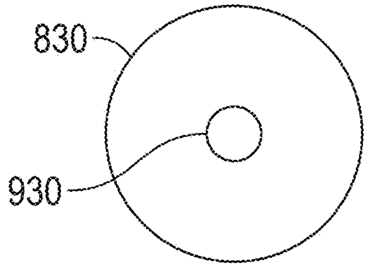
FIGS. 9A-9D illustrate front views of exemplary embodiments of the infusion ports associated with the systems shown in FIGS. 8A-8D.

FIG. 9A illustrates a front view of an exemplary infusion port suitable for use in a system shown in FIG. 8A.

In this illustrated embodiment, port 830 may include an area 930 that is attached to catheter 820 extending in a direction perpendicular to a plane of the page the figure is drawn on and, thus, is not shown.

As discussed previously with regard to connector 130, area 930 may include a screw thread connector, for example, which allows for the connection to a matching connector that is incorporated onto an end of tubing 875. Alternatively, area 930 may comprise a puncturable material (e.g., rubber) that allows for the insertion of a needle, to transfer fluid from reservoir 850.

Figure 9B:
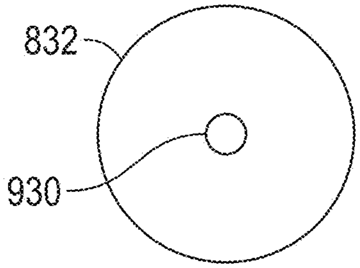

FIG. 9B illustrates a front view of an exemplary infusion port suitable for use in a system shown in FIG. 8B.

In this illustrated embodiment, infusion port 832 may include area 930 that is attached to catheter 120 extending in a direction perpendicular to a plane of the page the figure is drawn on and, thus, is not shown.

As discussed previously, area 930 may include a screw thread connector, for example, or a puncturable material for the insertion of a needle, which allows for the transfer of fluids from both reservoir 150 and reservoir 850 to catheter 120.

In one aspect of the invention, area 930 may comprise a puncturable material that allows for the concurrent insertion of needles connected to corresponding ones of reservoir 150 and second reservoir 850 that allows for the transfer of fluids to catheter 120.

Figure 9C:
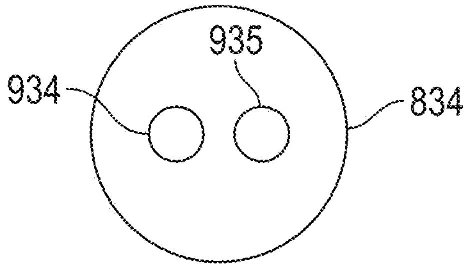

FIG. 9C illustrates a front view of an exemplary infusion port suitable for use in a system shown in FIG. 8C.

In this illustrated embodiment, port 834 may include a first area 934 and a second area 935 that are attached to catheter 821 and 823, respectively. Catheters 821, 823 extend in a direction perpendicular to a plane of the page the figure is drawn on and, thus, are not shown.

Similar to the discussion with regard to area 930, areas 934 and 935 may include a screw thread connector, for example, or a puncturable material suitable for the insertion of, and penetrable by a needle, to allow for the transfer of one or more fluids from reservoirs 150, 850 to respective ones of catheter 821, 823. In this illustrated example, the flow of fluids may be controlled to allow for the creation of a solution within mixing area 827 that satisfies one or more of criteria (e.g., baricity) prior to the distribution of the solution through openings 822*a*-822*d*.

Figure 9D:
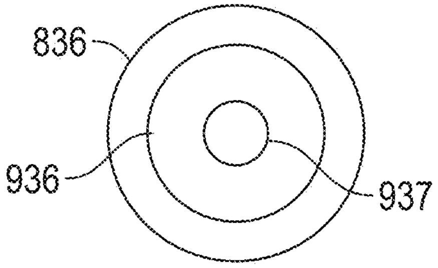

FIG. 9D illustrates a front view of an exemplary infusion port suitable for use in a system shown in FIG. 8D.

In this illustrated embodiment, port 836 may include a first area 936 and a second area 937, wherein the second area is contained within first area 936. First area 936 allows for the transfer of fluid to catheter 829, which extends in a direction perpendicular to a plane of the page the figure is drawn on and, thus, is not shown. Second area 937 allows for the transfer of fluid to catheter 828 and also is not shown.

Similar to area 930, areas 936 and 937 may include a screw thread connector, for example, or a puncturable material that allows for the insertion of a needle, to transfer one or more fluids from reservoirs 150, 850 to respectively ones of catheter 828, 829. In this illustrated aspect, fluids from reservoirs 150, 850 are mixed together in mixing area 827 to form a solution that satisfies one or more criteria (e.g., baricity) prior to the distribution of the solution through openings 822*a*-822*d*.

Figure 10:
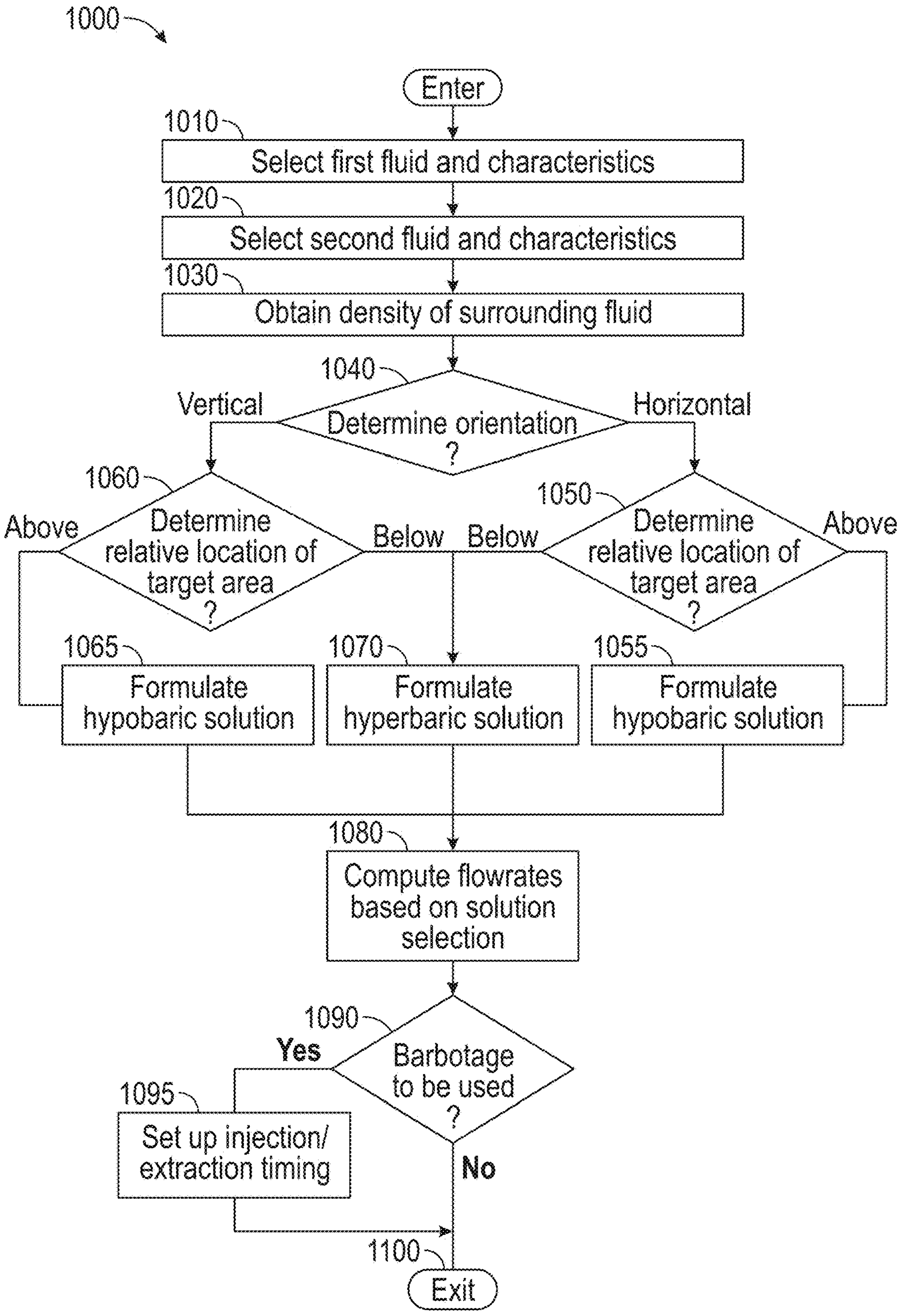
FIG. 10 illustrates a flowchart of an exemplary processing for determining fluid distribution in accordance with the principles of the invention.

FIG. 10 illustrates a flowchart of an exemplary process 1000 for determining fluid delivery in accordance with the principles of the invention.

In this illustrated flowchart, processing selects a first fluid, at step 1010, and a second fluid, at step 1020. The characteristics (e.g., density, viscosity, etc.) of each of the first fluid and the second fluid may be obtained from known information or derived from known information.

At step 1030, a characteristic of a surrounding fluid within a cavity may be obtained or derived from known information.

At step 1040 a determination is made with regard to the orientation of a catheter, wherein if a vertical orientation is determined, processing proceeds to step 1060, wherein a location of a desired target area with respect to the inserted catheter is determined.

If the desired target area is determined to be higher than a position of a distal (i.e., fluid distribution) end of the inserted catheter, then processing proceeds to step 1065 where a hypobaric solution based on the characteristics of the first fluid and the second fluid is formulated. The hypobaric solution formulation may include a ratio of the first fluid to the second fluid. The hypobaric solution formulation may include a flowrate of the first fluid and another flowrate of the second fluid from respectively ones of a reservoir 150 and a second reservoir 850. Processing proceeds to step 1080.

Returning to step 1060, if the target area is determined to be below a position of the distal end of the inserted catheter, then processing proceeds to step 1070 wherein a hyperbaric solution based on the characteristics of the first fluid and the second fluid is formulated. The hyperbaric solution formulation may include a ratio of the first fluid to the second fluid. The hyperbaric solution formulation may include a flowrate of the first fluid and another flowrate of the second fluid from respectively ones of a reservoir 150 and second reservoir 850. Processing proceeds to step 1080.

Returning to step 1040, if a horizontal positioning is determined, then processing proceeds to step 1050, wherein a location of a target area is determined with respect to a distal end of the inserted catheter. If the target area is determined to be above the location of the catheter, then processing proceeds to step 1055, wherein a hypobaric solution is formulated in a manner similar to that discussed with regard to step 1065. Processing proceeds to step 1080.

However, if the target area is determined to be below the inserted catheter, then processing proceeds to step 1070 to formulate a hyperbaric solution. Processing proceeds to step 1080.

At step 1080 a flowrate associated with the first fluid and another flowrate associated with the second fluid may be computed to obtain the solution formulations associated with steps 1055, 1065 and 1070. Processing then proceeds to step 1090, wherein a determination is made whether barbotage (an insertion/extraction process in accordance with the present disclosure) is to be utilized.

If barbotage is to be utilized then processing proceeds to step 1095, wherein a timing of fluid injection and fluid extraction of the formulated solution is determined in a manner as previously discussed.

Processing proceeds to step 1100, wherein processing is ended.

If barbotage, at step 1090, is determined not to be utilized, then processing proceeds to step 1100, wherein processing is ended.

In one aspect of the invention, a sensor may be incorporated into, for example, systems 800, 802, 804, 806, etc., that may be utilized to determine an orientation of the target area 190 with respect to a point of insertion of, for example, catheter 120 (820, 821, 823, 825, 828, 829). In accordance with one application of the invention disclosed, wherein a formulated medication solution is to be provided to an intrathecal cavity of a patient, an orientation of the patient (i.e., vertical, horizontal) may, in part, determine an orientation of target area 190 with respect to the insertion point of, or the distribution point (e.g., offices 122*a*-122*d*) of catheter 120.

Accordingly, the orientation of a patient may further provide an estimation of a location of target area 190, which may then be utilized to determine a baricity of a solution formulated between a medication and a second fluid (e.g., saline, dextrose, etc.). In one aspect of the invention, the information provided by one or more sensors may comprise information associated with at least one of acceleration data and/or gyroscopic data. In one aspect of the invention, interface 165 may provide a means for the input of a patient orientation that may be used by processor 160 to determine, for example, an appropriate fluid flow rate to achieve a desired baricity.

In one aspect of the invention, the baricity of the distributed medication solution may be dynamically altered as one or more sensors provide orientation information to processor 160, wherein processor 160 may utilize the sensor information to adjust one or more of the distribution of fluids (e.g., flow rates) and the timing of fluid distribution from corresponding ones of reservoirs 150, 850.

In one aspect of the invention, distribution system 800, 802, 804, 806 may be implanted within a patient, to whom medication is to be provided to the intrathecal cavity. In this example, a single extension catheter 175 may transfer fluids from externally mounted reservoirs to the internally implanted distribution system(s). Internal implantation of the illustrated distribution system is advantageous as it allows a patient to be mobile while receiving a required medication. As discussed, one or more sensors may provide information to processor 160 to alter the flow of, or the timing of, the delivery of required medication in response to sensor information representing a change in patient position or spatial orientation. Alternatively, distribution system 800 (for example), may represent a standalone device that allows for the distribution of required medications while the patient is in a fixed orientation (e.g., in a doctor's office or hospital setting). In this aspect, sensor information regarding patient orientation may be included in a computation for the required flow, or timing, of medication to the patient.

Accordingly, the location of the target area with respect to a point of insertion of catheter 120 into the space and the orientation of a patient (e.g., horizontal, vertical) may further be utilized to determine a desired baricity and an orientation of the inserted catheter into the space. For example, with a patient in a vertical position and an estimated or determined location of the target area 190 with respect to the point of insertion of catheter 120, catheter 120 may be inserted at an upward angle to administer a hypobaric solution. Similarly, with a patient in a vertical position, and an estimated or determined location of the target area 190 as being below the insertion point, catheter 120 may be inserted at a slightly downward orientation to deliver a hyperbaric solution to target area 190.

Accordingly, knowledge of an orientation of a patient may be utilized to determine an orientation of the insertion of catheter 120 to position a distal end of catheter 120 closer to target area 190. Thus, a therapeutic solution provided through catheter 120 may arrive at target area 190 more rapidly. For example, with regard to distribution of medication to the intrathecal cavity, catheter 120 is typically inserted such that catheter 120 is oriented within the intrathecal cavity along, or in-line with, the spine of the patient. Thus, FIGS. 3A-3C illustrate examples of the insertion of catheter 120 into a patient oriented in a horizontal position and FIGS. 6A-6C illustrate examples of the insertion of catheter 120 in a vertically oriented patient.

Although not shown, it would be recognized by those skilled in the art that if it is determined that the target area is substantially adjacent to the distributing end of the inserted catheter, the illustrated processing may be altered to formulate an isobaric solution.

In addition, as discussed previously, the medication morphine is substantially isobaric with respect to CSF. In the case of prescribing a formulation comprising morphine, if it is determined that the target area 190 is substantially adjacent to the distributing end of the inserted catheter, then only a single fluid (i.e., morphine) may be distributed to provide for a maximum amount of medication to reach target area 190.

Although the invention has been described with regard to adaptors (i.e., FIGS. 9A-9D) external to distribution systems 800, 802, 804, 806, it would be recognized that the illustrated adaptors may be included within distribution system 800, 802, 804, 806, such that only a single extension catheter 175 need be provided with the illustrated catheter configurations (FIGS. 8A-8D).

Figure 11:
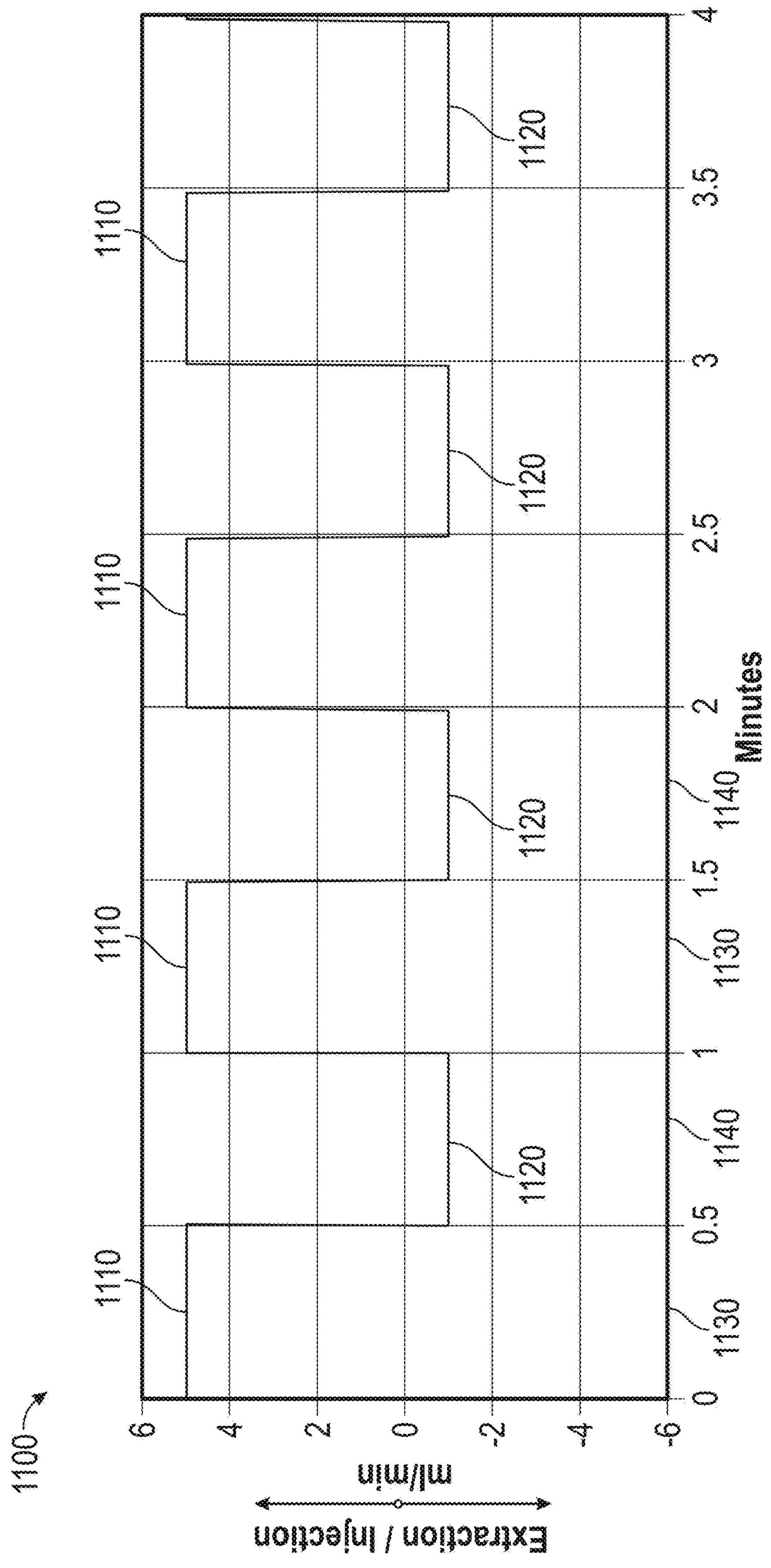
FIG. 11 illustrates an exemplary fluid flow distribution/extraction timing diagram in accordance with the principles of the invention.

FIG. 11 illustrates an exemplary fluid flow distribution/extraction timing diagram in accordance with one aspect of the invention.

In this exemplary timing diagram 1100, a timing, determined from the calculations performed with regard to Equations 12 and 13, associated with fluid injection 1110 and fluid extraction 1120 is shown. In this illustrated example and using the previously discussed parameters of F_net, F_inject and F_extract, a fluid injection of 5 ml/min is performed for a first time period 1130 and a fluid extraction of 1 ml/min is performed for a second period of time 1140. The first and second time periods being substantially equal since the I:E ratio has been selected to be 1:1.

However, such timing may not be advantageous as this example timing may fail to provide sufficient time for the injected fluid to disperse within the surrounding fluid such that the aspirated fluid may not include a mixture of the injected fluid and the CSF.

Figure 12:
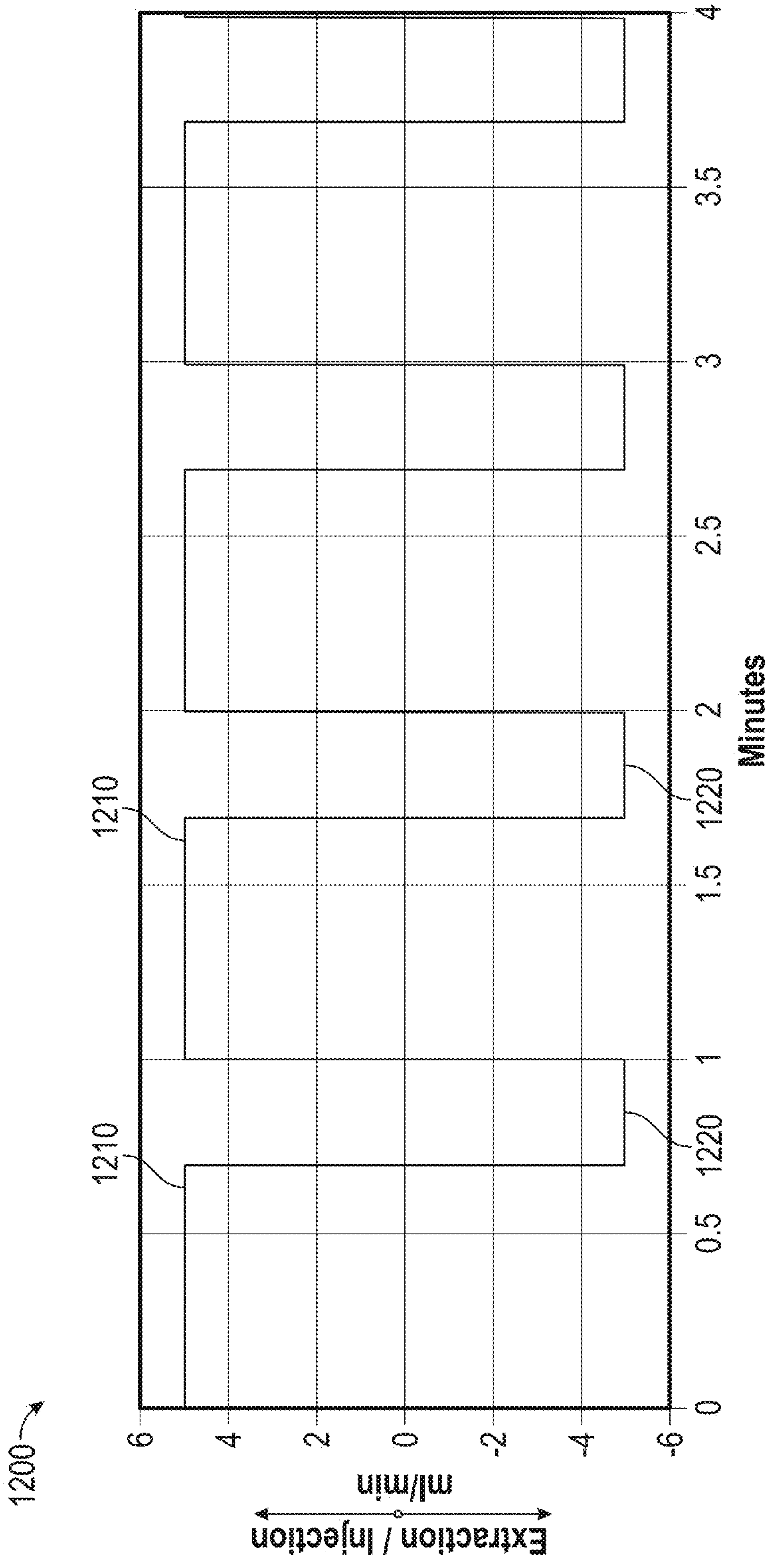
FIG. 12 illustrates a second exemplary fluid flow distribution/extraction timing diagram in accordance with the principles of the invention.

FIG. 12 illustrates a second exemplary fluid flow distribution/extraction timing diagram in accordance with the principles of the invention.

In this illustrated timing diagram 1200, a timing, determined from the calculations performed with regard to Equation 12 and 13, associated with a fluid injection 1210 and fluid extraction 1220 is shown. As discussed previously with reference to FIG. 11, wherein the F_extract is selected to be substantially the same as F_inject, a I:E is determined to be 2.33 and with corresponding flow rates in a ratio of 2:086.

As shown, the timing of fluid injection is slightly greater than twice that of the timing of fluid extraction so as to satisfy the I:E flowrate ratio of 2:086.

FIGS. 13-18 illustrate examples of an exemplary Graphic User Interface (GUI) for an intuitive determination of fluid flow distribution/extraction timing in accordance with the principles of the invention.

Figure 13:
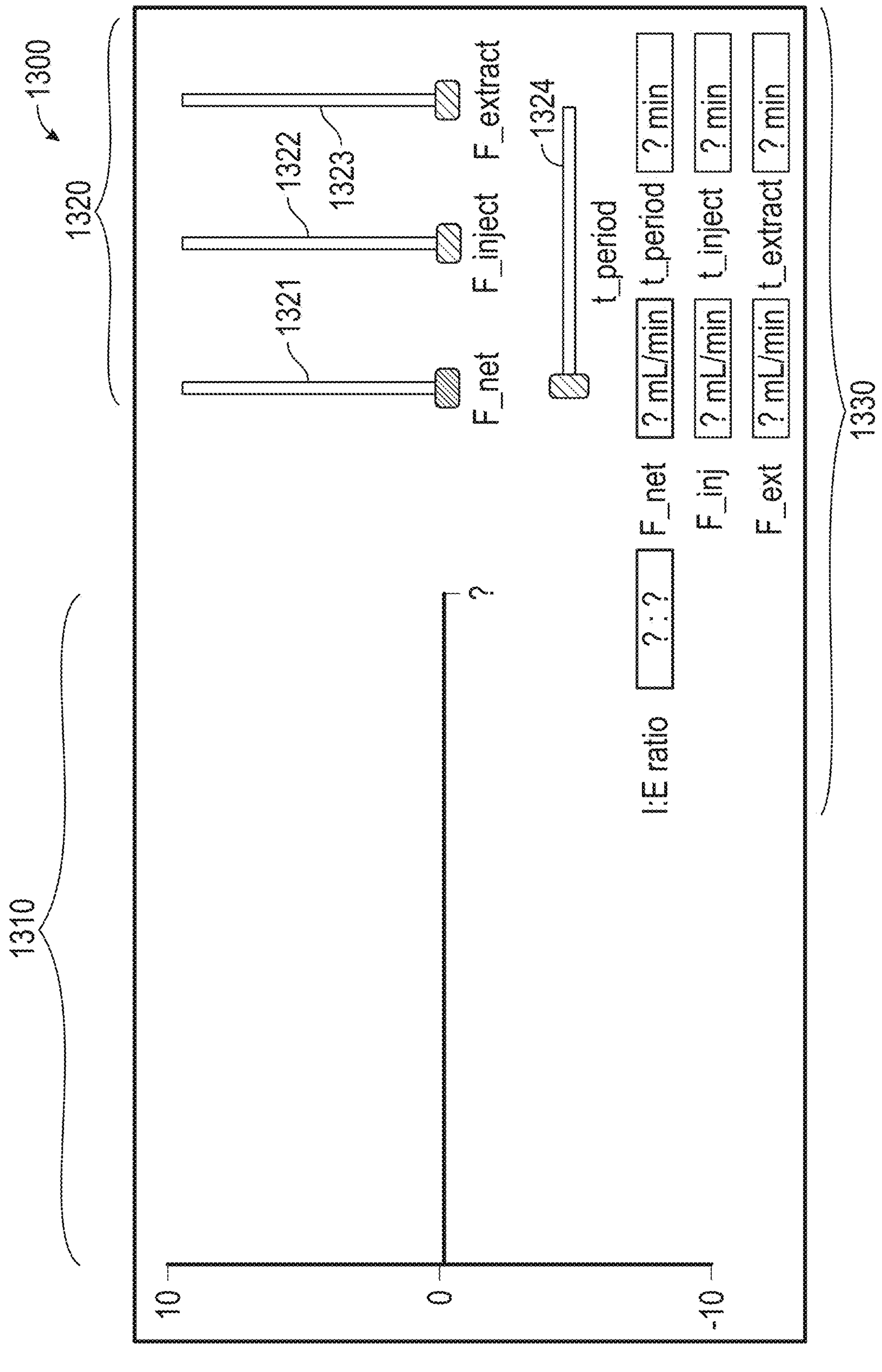
FIGS. 13-18 illustrate examples of an exemplary Graphic User Interface for an intuitive configuration and determination of fluid flow distribution/extraction timing in accordance with the principles of the invention.

FIG. 13 illustrates an exemplary embodiment of a GUI 1300 that may be utilized to provide information to processor 160 through interface 165 to establish parameters associated with a distribution of fluids in accordance with the principles of the invention.

The disclosed methods may be embodied as a computer software application stored at least in part on a non-transitory information storage medium and made available via an internet-accessible service for download to consumer electronic devices such as mobile phones, gaming consoles, tablet computers, desktop computers, smart appliances, or other programmable devices having access to processor 160 through interface 165 enabling the display of information and user specification of configuration parameters for the disclosed methods. Examples of suitable internet-accessible services include the Apple Store, Google Play, and other sites that make software applications and other downloads available for purchase or license.

An implementation may be configured to receive one or more prescriptions for one or more specified baricity or barbotage protocol using one or more fluids. The implementation may receive the one or more prescriptions through interface 165, for example. The implementation may be configured to activate and use the one or more prescriptions in accordance with the present disclosure. The implementation may activate one baricity and/or barbotage prescription at one time and activate another baricity and/or barbotage prescription at another time. In an illustrative example the implementation may be configured through interface 165 to use one baricity and/or barbotage prescription when a first patient spatial orientation is detected based on sensor information. The implementation may be configured through interface 165 to use another baricity and/or barbotage prescription when a second patient spatial orientation is detected based on sensor information. The implementation may be configured to switch between a plurality of baricity and/or barbotage prescriptions in response to sensor information comprising an indication the patient spatial orientation changed.

Various implementations may be configured to detect patient spatial orientation and patient spatial position and adjust baricity and/or barbotage based on the changed spatial orientation or changed position, to provide effective treatment for the patient using a baricity or barbotage protocol determined by the processor 160 based on the changed orientation or position. For example, the implementation may use one prescription when a patient is horizontal and another prescription when the patient is vertical. Various implementations may be configured to alternate or cycle between aspiration and infusion to agitate medication delivered and optimize effect/extent. Various implementations may be configured to adjust baricity of a therapeutic solution in response to a change in patient position determined as a function of sensor information. Some implementations may be configured with a GUI configured to permit a patient to select a baricity and/or barbotage prescription from a plurality of prescriptions on demand, wherein the patient may select and activate a prescription the patient found effective in a particular position or orientation in the past.

GUI 1300 comprises one or more of graph section 1310, operational section 1320 and information section 1330, wherein graph section 1310 may be utilized to visually present a timing of a proposed fluid injection/fluid extraction cycle, based on information provided in operational section 1320 and/or information section 1330.

Operational section 1320 comprises a means to input one or more of the parameters to determine a fluid flow rates, as discussed herein. For example, operational section 1320 may comprise selection mechanisms 1321, 1322, 1323, associated with parameters F_net, F_inject and F_extract, respectively. Also shown is selection mechanism 1324 associated with a time period or cycle (t_period) parameter that may be used to select an overall period of time for one or more of the processes of fluid injection and fluid extraction.

In the illustrated aspect of GUI 1300, selection means 1321, 1322, 1323 comprise measurement bars including sliding cursors that allow for selection of a data input value. Although measurement bars are shown, it would be recognized that selection mechanisms 1321-1324 may also comprise buttons (up/down button) to increase or decrease a corresponding parameter, or knobs that may be used to set a corresponding parameter.

Information section 1330 provides digital representations of the values input from corresponding ones of selection mechanisms 1321-1324. Alternatively, specific values may be entered into corresponding elements of information section 1330 that may be used in the calculations of fluid rates.

Figure 14:
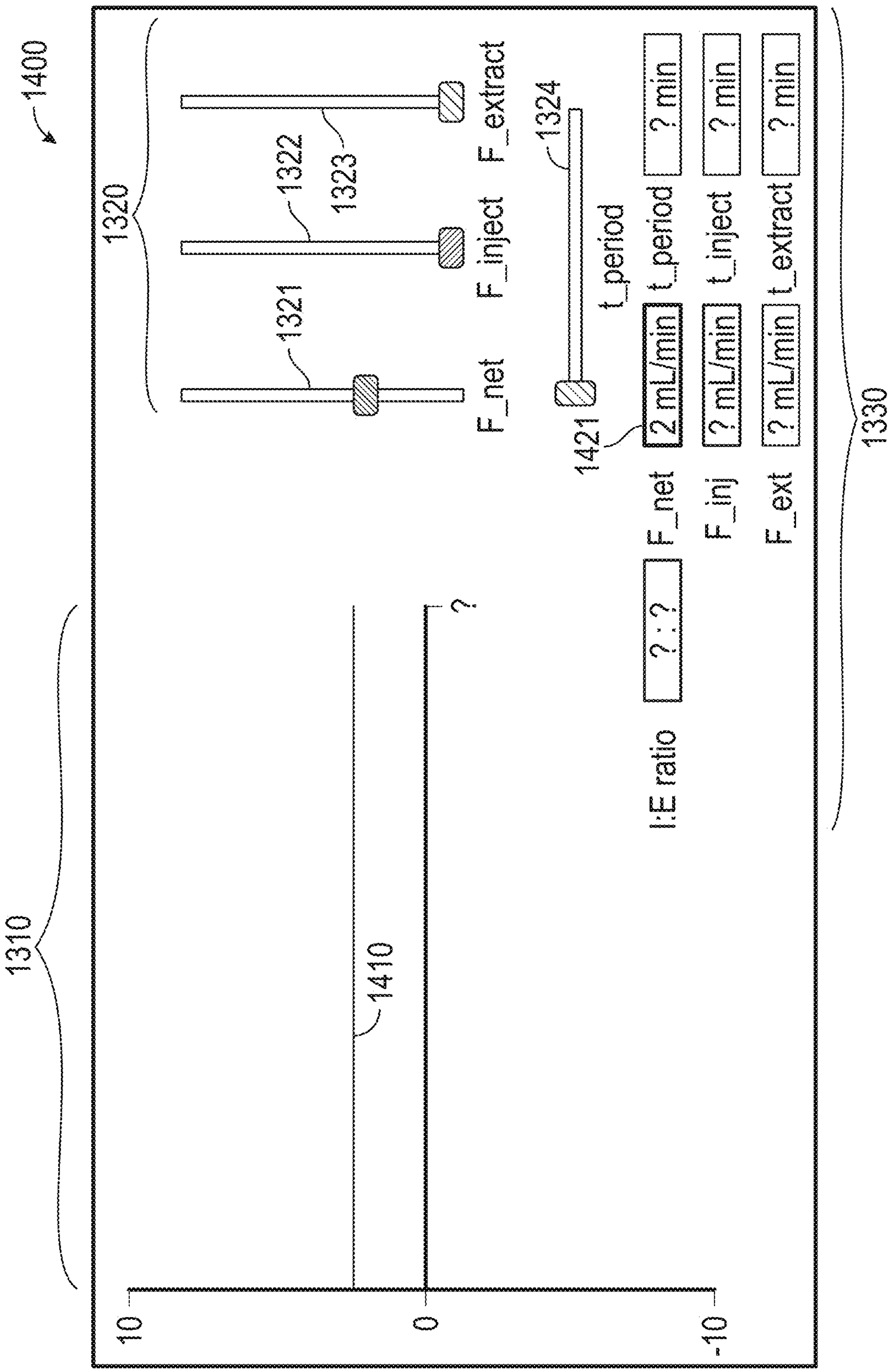

FIG. 14 illustrates an example 1400 of an interaction of GUI 1300 with regard to inputting of a first parameter in accordance with the principles of the invention.

In this illustrated example, input of a parameter associated with a desired F_net is provided to processor 160 by the entry of a first parameter to a desired value (e.g., by the alteration of a position of a sliding cursor associated with means 1321). Concurrently, a visual presentation 1410 of the desired F_net is displayed in graphic section 1310. In addition, the selected value is presented in corresponding section 1421 within operational section 1330. Alternatively, a desired value may be inputted into section 1421 and a position of the cursor associated with measurement bar 1321 may be altered to represent the inputted value.

Figure 15:
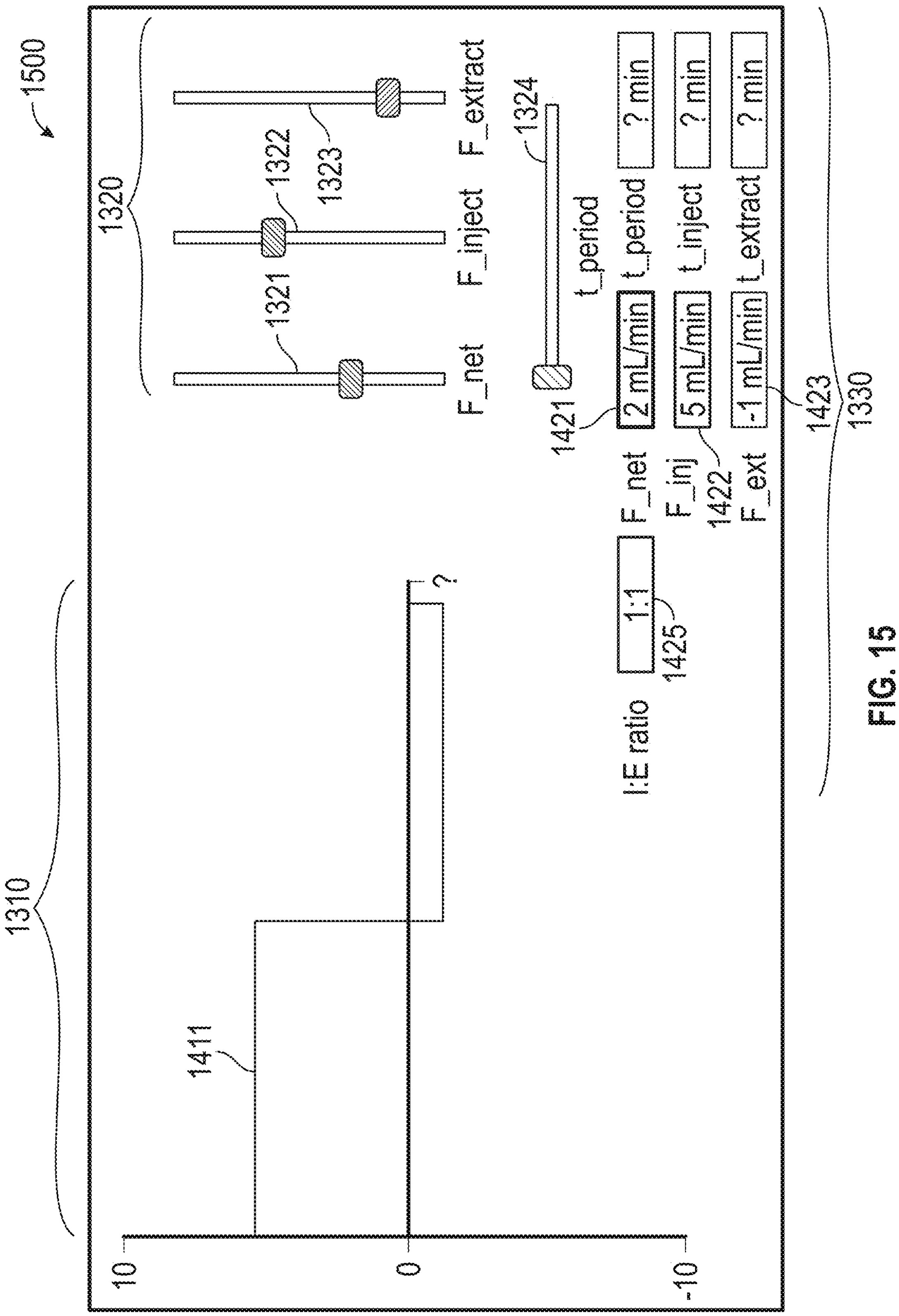

FIG. 15 illustrates a further example of an interaction of GUI 1300 with regard to inputting of a second parameter in accordance with the principles of the invention.

In this illustrated example, input of a second parameter is provided to processor 160 by the entry of the second parameter to a desired value. In this illustrated example, the second parameter is represented by a desired value of F_inject. Concurrently, a digital representation of the input or desired value in presented corresponding section 1422. Alternatively, a value may be entered into section 1422 and a position of cursor associated with measurement bar 1322 may be altered.

In addition, as F_net, F_inject and F_extract are related, as expressed in Equation 12, a concurrent presentation of F_extract may be presented in corresponding section 1423, and a default I:E ratio (i.e., 1:1) may be presented in corresponding section 1425. In addition, an exemplary timing 1411 of F_inject and F_extract may be graphically presented in graphic section 1310 to provide a visual display of an effect of the input variables. In this illustrated example, the default I:E ratio is pre-selected as 1:1, and the timing of fluid injection and fluid extraction is shown to be substantially equal.

Figure 16:
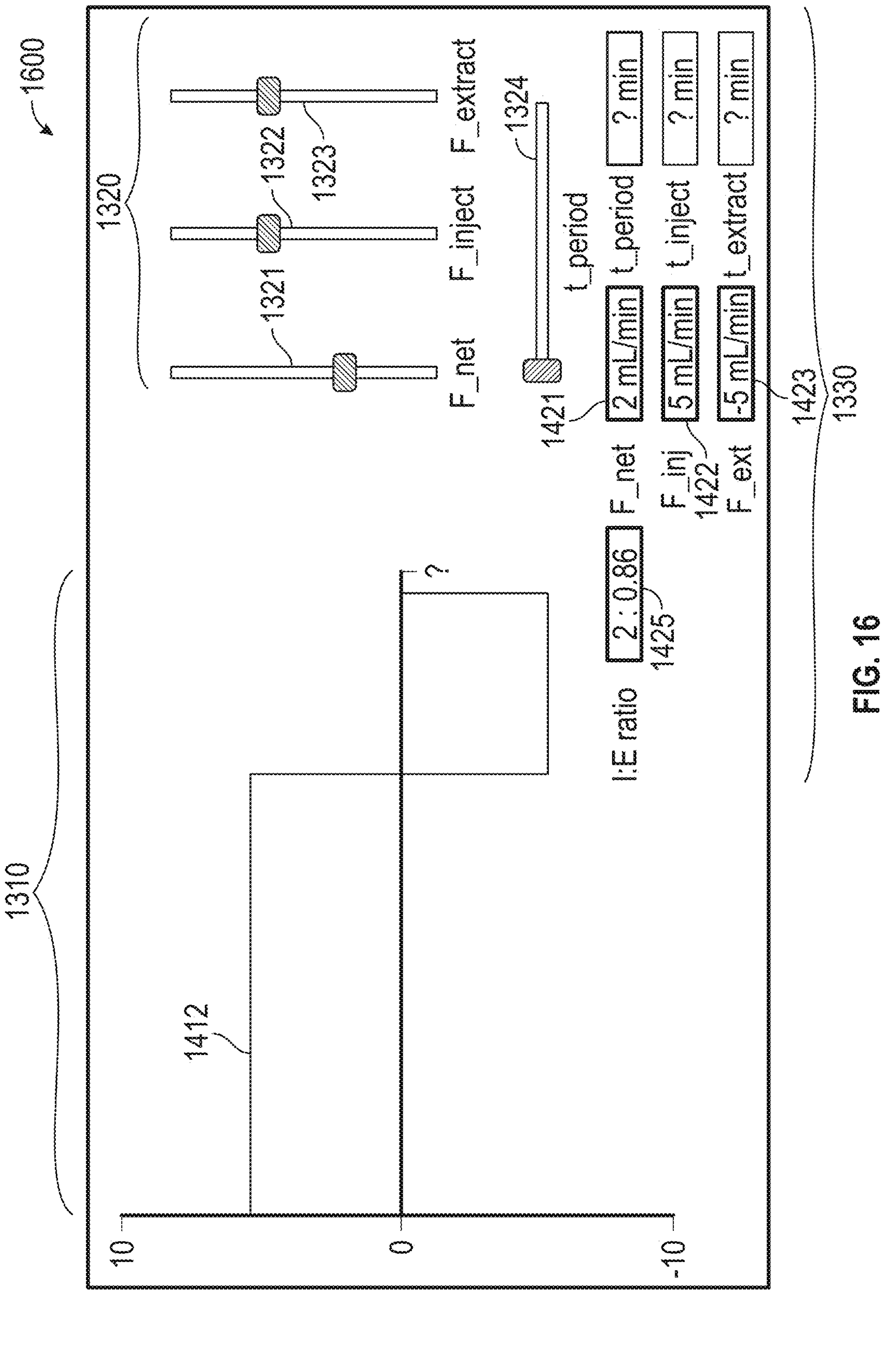

FIG. 16 illustrates a further example 1600 of an interaction of GUI 1300 with regard to modification of at least one parameter in accordance with the principles of the invention.

In this illustrated example, the original default condition is over-ridden by the input of a third parameter to processor 160. In this illustrated example, the third parameter is represented by a desired value of F_extract. Accordingly, with the alteration of the value of F_extract determined by Equation 13, the input of a new F_extract alters the injection and extract ratio, as discussed with regard to Equation 17.

In this illustrated example a desired input F_extract is inputted into processor 160 through movement of a cursor associated with measurement bar 1323. Concurrently, the desired input value of F_extract is shown in corresponding section s shown 1423 and a new I:E ratio is computed and presented in corresponding section 1425. Further illustrated is graphic presentation 1412 of a timing associated with the computed I:E ratio wherein time of fluid injection is slightly greater than a time of fluid extraction as was previously discussed.

Figure 17:
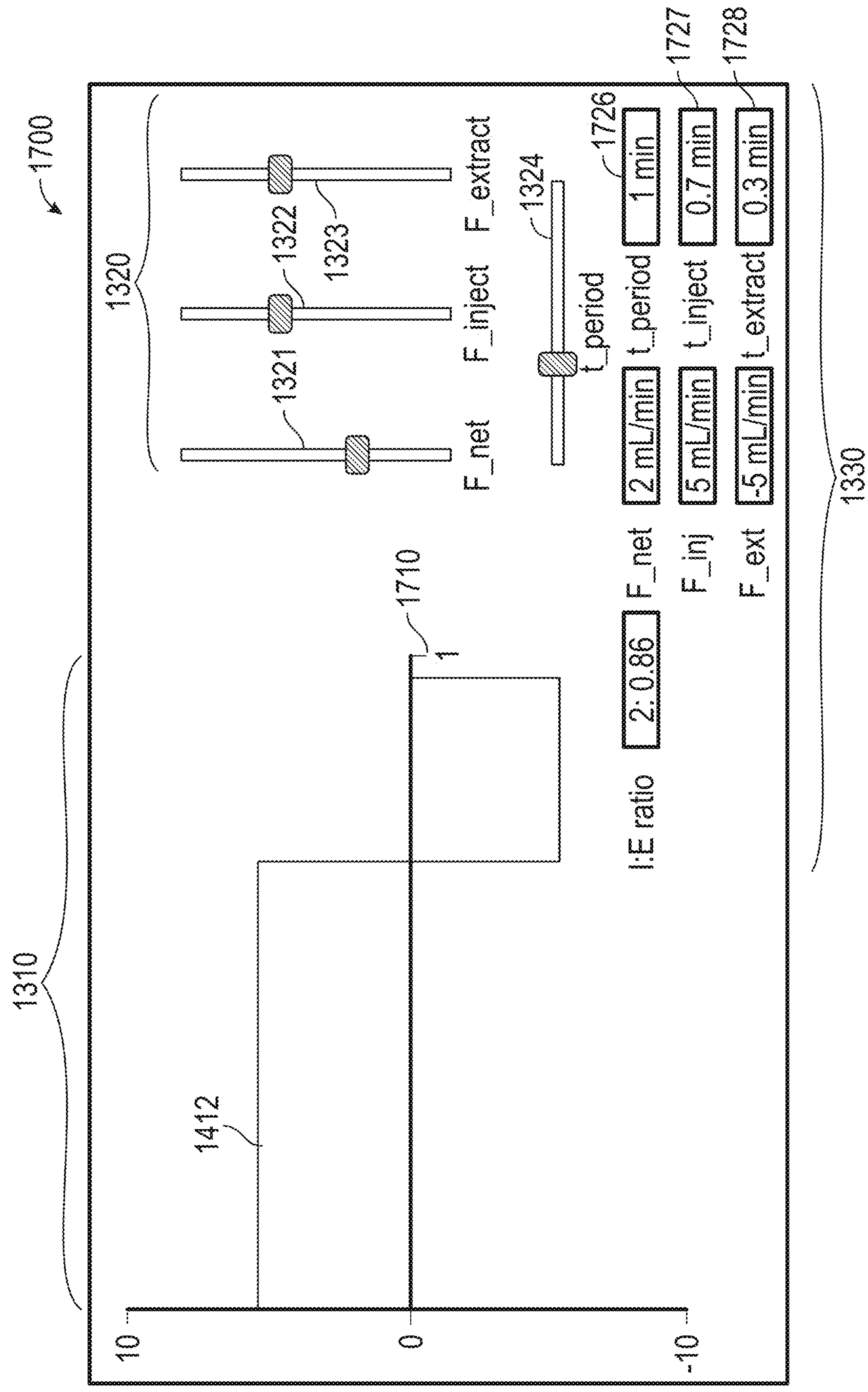

FIG. 17 illustrates a further example 1700 of an interaction of GUI 1300 with regard to inputting of a time parameter in accordance with the principles of the invention.

In this illustrated aspect, a time period (t_period) may be established as a cycle of fluid injection and extraction, wherein a desired value may be entered into processor 160. In this illustrated example, a time period may be entered visually, through means 1324 or digitally through corresponding section 1726. In this illustrated example, entry of a time period of 1 minute is displayed 1710 on graphic presentation 1412. Furthermore, corresponding times of fluid injection and fluid extraction may be shown in corresponding sections 1727 and 1728, respectively. Injection and extraction times may be determined in part based on the I:E ratio and the cycle time period (t_period).

Figure 18:
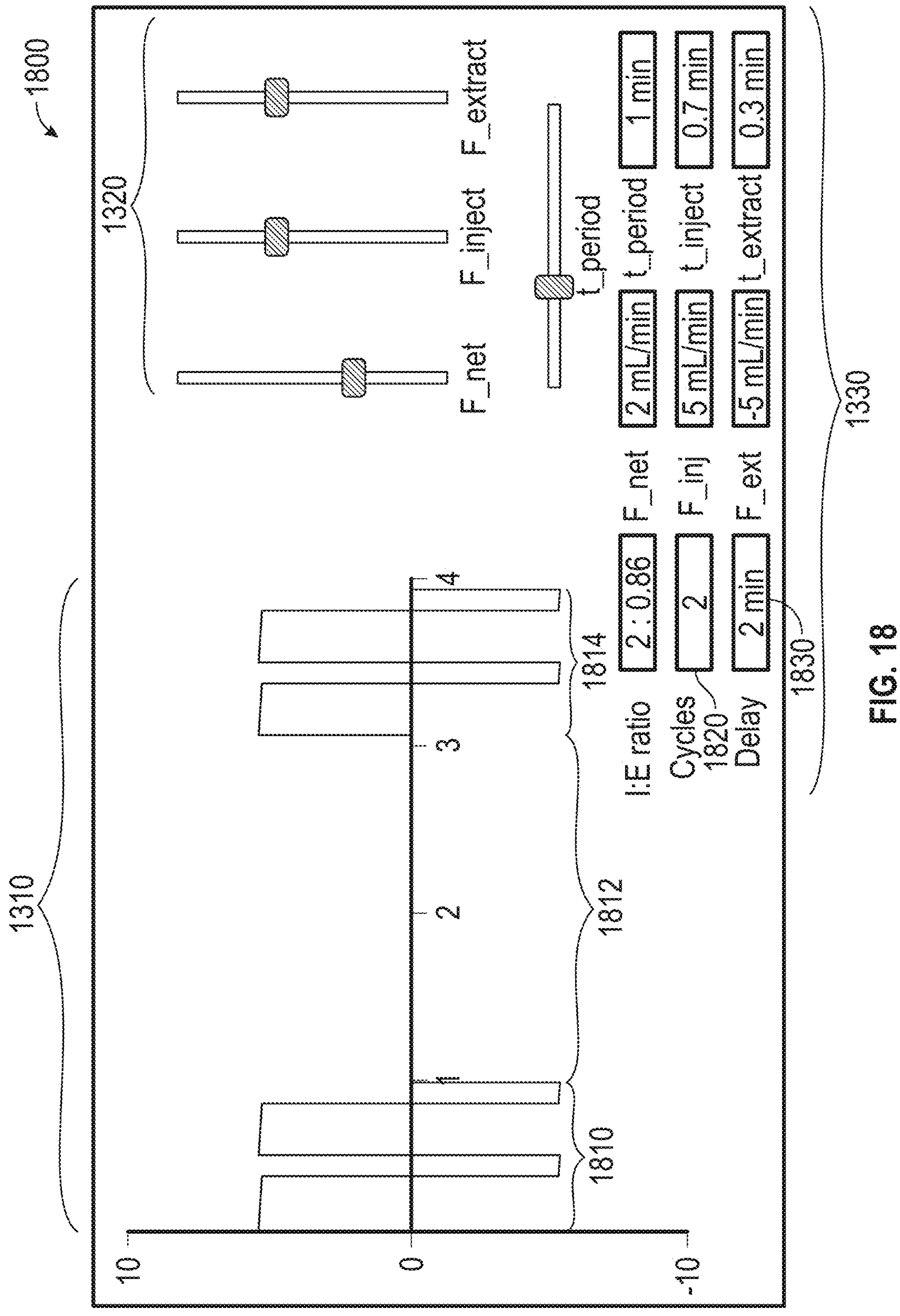

FIG. 18 illustrates a further example 1800 of an interaction of GUI 1300 with regard to inputting additional parameters in accordance with the principles of the invention.

In this illustrated example, after input of a t_period to define a fluid injection/extraction period or cycle time, an overall process schedule may be determined through GUI 1300. In one aspect of the invention, after a cycle time has been established one or more additional parameters may be inputted to define a process schedule. For example, entries for a number of cycles per time period (or cycle time) may allow configuring a cycle rate for the illustrated injection/extraction cycle within each time period. Entry section 1820 allows input of the number of cycles/period. In this illustrated example, two (2) cycles of injection/extraction per period (e.g., 1 minute) is desired. In addition, a delay feature may be desired, wherein a delay in the delivery of medication is provided. In this illustrated example, a delay of two (2) minutes between medication delivery time periods is entered into corresponding section 1830.

Further illustrated in FIG. 18 is a graphic representation of the proposed medication scheduling wherein two cycles of injection/extraction are shown within a first t_period 1810, a delay of medication for the desired two minutes 1812 and two further cycles of medication injection/extraction in a second t_period 1814.

The illustrated medication schedule may continue for a fixed period of time (e.g., 1 day, 1 week, etc.). Alternatively, one or more additional parameters (not shown) may be inputted that allow for additional scheduling values. For example, the illustrated schedule of four (4) minutes duration may be performed once per hour or once per day or once per every other day, etc. The ability to incorporate such additional scheduling parameters would be within the knowledge of those skilled in the electrical arts and as such need not be discussed in detail herein.

Although various features have been described with reference to the Figures, other features are possible.

For example, a method implementation may comprise: fluidly coupling at least one lumen with a plurality of reservoirs, each reservoir of the plurality of reservoirs retaining at least one first fluid, wherein one fluid of the at least one first fluid comprises a medication; determining a baricity of the at least one first fluid within each reservoir of the plurality of reservoirs; controlling a release of the at least one first fluid from each reservoir of the plurality of reservoirs; creating a solution comprising the at least one first fluid, wherein a release rate of each fluid of the at least one first fluid is determined as a function of a targeted baricity for the solution; and directing the solution into a space containing a second fluid, wherein the targeted baricity of the solution determines distribution of the solution with respect to the second fluid contained within the space.

The space may be an intrathecal space and the second fluid may be a cerebrospinal fluid (CSF).

The at least one lumen may be encapsulated by another lumen.

The at least one lumen may comprise: a plurality of lumens, wherein at least one lumen of the plurality of lumens may be in fluid communication with at least one reservoir of the plurality of reservoirs.

The targeted baricity of the solution may be selected to enable a gravitationally upward movement of the solution within the space.

The targeted baricity of the solution may be selected to enable a gravitationally downward movement of the solution within the space.

The plurality of lumens may be encapsulated within a sheathing.

At least one lumen of the plurality of lumens may be encapsulated within another lumen of the plurality of lumens.

Each fluid of the at least one first fluid within the plurality of reservoirs may have a distinct specific gravity or density.

A system implementation may comprise: at least one catheter insertable into a space; a plurality of pumps, wherein each pump of the plurality of pumps is fluidly coupled to the at least one catheter and each pump is configured to release at least one first fluid from one reservoir of a plurality of reservoirs through the at least one catheter into the space, thereby creating a solution in the space; and a processor in communication with each pump of the plurality of pumps, wherein the processor is configured to control operation of each pump of the plurality of pumps individually to release the at least one first fluid from the plurality of reservoirs through the at least one catheter at a plurality of known rates, and the processor is further configured to select each rate of the plurality of known rates to achieve a targeted baricity of the solution.

The targeted baricity of the solution may enable a gravitationally upward movement of the solution within the space.

The targeted baricity of the solution may enable a gravitationally downward movement of the solution within the space.

The at least one catheter may be encapsulated within a sheathing.

At least one catheter may be encapsulated within another catheter.

Each fluid of the at least one first fluid within the plurality of reservoirs may have a distinct specific gravity or density.

A system implementation may comprise: at least one catheter removably insertable into an intrathecal space; a plurality of reservoirs in fluid communication with the at least one catheter, wherein the plurality of reservoirs is configured to release at least one first fluid to the at least one catheter, wherein the at least one first fluid comprises a medication; at least one pump of a plurality of pumps in communication with at least one reservoir of the plurality of reservoirs, wherein the at least one pump applies force to the at least one first fluid to release the at least one first fluid at a known rate; and a processor in communication with each pump of the plurality of pumps, wherein the processor is configured to control operation of each pump of the plurality of pumps individually to release the at least one first fluid from the plurality of reservoirs through the at least one catheter at a plurality of known rates, and the processor is further configured to select each rate of the plurality of known rates to achieve a targeted baricity of a solution comprising a plurality of released first fluids.

The at least one catheter may be encapsulated with a sheathing.

The at least one catheter may be encapsulated by another catheter.

The targeted baricity of the solution may be selected by the processor to enable a gravitationally upward movement within the intrathecal space.

The targeted baricity of the solution may be selected by the processor to enable a gravitationally downward movement within the intrathecal space.

A method implementation may comprise: fluidly coupling a first end of at least one lumen to each reservoir of a plurality of reservoirs, wherein each reservoir of the plurality of reservoirs contains a first fluid; configuring a second end of the at least one lumen in fluid communication with a space containing a second fluid; distributing, for a first period of time, the first fluid from at least one reservoir of the plurality of reservoirs through the at least one lumen into the space; aspirating, for a second period of time, from the space through the at least one lumen into the at least one reservoir, a fluid combination of the second fluid from the space and at least one first fluid, wherein the fluid combination mixes with the first fluid within the at least one reservoir; and alternately distributing into the space, for the first period of time, and aspirating into the at least one reservoir, for the second period of time, mixtures of the fluid combination.

The at least one lumen may be a plurality of lumens, and each lumen of the at least one lumen may have at least a first end in fluid communication with the space.

The at least one lumen may be encapsulated within a sheathing.

The plurality of lumens may be arranged concentrically.

A rate of aspiration of the fluid combination may be determined as a function of a targeted net flow and a rate of distributed fluid flow.

The rate of distributed fluid flow may be greater than the targeted net flow of fluid.

A ratio of the first period of time to the second period of time may be determined by the processor as a function of the rate of aspiration.

A system implementation may comprise: a plurality of reservoirs, each reservoir of the plurality of reservoirs containing a known fluid therein; a plurality of pumps fluidly coupled with the plurality of reservoirs, wherein at least one pump of the plurality of pumps is a bidirectional pump; at least one lumen fluidly coupled with each reservoir of the plurality of reservoirs; and a processor operably coupled with the plurality of pumps, the processor configured to: inject fluid contained in at least one reservoir of the plurality of reservoirs into a space through the at least one lumen as a function of configuring at least one bidirectional pump of the plurality of pumps to operate in a first direction, for a first period of time; after the first period of time, extract fluid from the space into at least one reservoir through the at least one lumen as a function of configuring the at least one bidirectional pump to operate in a second direction, for a second period of time; and continuously mix injected fluid and extracted fluid in the at least one reservoir and the space by alternating fluid injection and fluid extraction as a function of configuring the at least one bidirectional pump to alternately operate in the first direction and the second direction.

The at least one lumen may be encapsulated within a sheathing.

The at least one lumen may be a plurality of lumens and the plurality of lumens may be arranged concentrically.

Some lumens of the plurality of lumens may be arranged concentrically around one lumen of the plurality of lumens.

A rate of extraction of fluid from the space may be determined by the processor based on a targeted net flow of injected fluid and a rate of flow from at least one reservoir of the plurality of reservoirs, and the fluid extracted from the space may be a combination of injected fluid and extracted fluid.

The rate of flow from at least one reservoir of the plurality of reservoirs may be greater than the targeted net flow.

A ratio of the first period of time to the second period of time may be determined by the processor based on a determined rate of extraction.

A system implementation may comprise: at least one catheter removably insertable into an intrathecal space; and a control system comprising: a plurality of reservoirs, wherein at least one of the at least one catheter is removably attachable to one reservoir of the plurality of reservoirs, wherein each reservoir of the plurality of reservoirs contains a distinct fluid and at least one reservoir contains a fluid comprising a medication; at least one pump fluidly coupled with each reservoir of the plurality of reservoirs, wherein at least one pump of the at least one pump is a bidirectional pump; and a processor operably coupled with the at least one pump, the processor configured to: inject fluid contained in at least one reservoir of the plurality of reservoirs into the intrathecal space through the at least one catheter as a function of configuring at least one bidirectional pump to operate in a first direction; extract fluid from the intrathecal space into at least one reservoir of the plurality of reservoirs through the at least one catheter as a function of configuring at least one bidirectional pump to operate in a second direction; and continuously mix injected fluid and extracted fluid in the at least one reservoir and the intrathecal space by alternating injection and extraction using the at least one bidirectional pump, wherein a fluid combination of injected fluid from the at least one reservoir and fluid within the intrathecal space is extracted from the intrathecal space though the at least one catheter into the at least one reservoir, and wherein a mixture of the fluid within the at least one reservoir and extracted fluid from the at least one reservoir is directed into the intrathecal space.

The at least one catheter may be a plurality of catheters.

The plurality of catheters may be enclosed within a sheathing.

The plurality of catheters may be concentrically arranged.

The processor may be further configured to: control the at least one bidirectional pump to operate in the first direction to inject fluid for a first period of time; and after the first period of time, control the at least one bidirectional pump to operate in the second direction to extract fluid for a second period of time, wherein start of the second period of time is delayed from an end time of the first period of time by a third period of time determined by the processor as a function of at least one characteristic of the mixture governing dispersion of the mixture in the intrathecal space.

The first period of time and the second period of time may be determined by the processor based on a determined rate of extraction of the fluid within the intrathecal space.

The rate of flow from each reservoir of the plurality of reservoirs may be greater than a targeted net flow of distributed fluids.

A method implementation may comprise: receiving sensor information indicating a spatial orientation of a patient; determining a relation of a target area location within an intrathecal space of the patient relative to an insertion point for distribution of a plurality of fluids; determining a targeted baricity of a solution comprising the plurality of fluids, wherein the targeted baricity is determined as a function of the spatial orientation information and an individual baricity of at least one fluid of the plurality of fluids; and controlling a distribution of the plurality of fluids into the intrathecal space, wherein a flowrate of each fluid of the plurality of fluids is determined based on the targeted baricity of the solution.

The method may further comprise altering the targeted baricity of the solution in response to receiving information comprising a change in the spatial orientation of the patient.

The method may further comprise adjusting the targeted baricity solution from a first prescribed baricity to a second prescribed baricity in response to receiving an indication the spatial orientation of the patient changed.

The received sensor information may further comprise data from at least one of an accelerometer, a gyroscope or a magnetometer.

The method may further comprise receiving the spatial orientation information as input to an implanted delivery device.

The targeted baricity of the solution may be selected to be hypobaric when the target area is gravitationally above the insertion point.

The targeted baricity of the solution may be selected to be hyperbaric when the target area is gravitationally below the insertion point.

The method may further comprise adjusting the baricity of the solution in response to a change in the spatial orientation of the patient.

A system implementation may comprise: at least one catheter configured to distribute a therapeutic solution to a target area within an intrathecal cavity; a control system comprising: a plurality of reservoirs, wherein each reservoir of the plurality of reservoirs is in fluid communication with at least one catheter, further wherein each reservoir is configured to contain a corresponding fluid; and a plurality of pumps in fluid communication with the plurality of reservoirs, wherein each pump of the plurality of pumps is configured to control a flow of fluid from one reservoir of the plurality of reservoirs; and a processor operably coupled with the plurality of pumps, the processor configured to: receive information regarding a spatial orientation of a patient; formulate a targeted baricity for a therapeutic solution determined as a function of the received information regarding the spatial orientation of the patient, a baricity of a fluid within at least one reservoir of the plurality of reservoirs and a fluid within the intrathecal cavity; control the plurality of pumps to provide an individual flowrate of fluid from each reservoir of the plurality of reservoirs to achieve the targeted baricity of the therapeutic solution; and direct the therapeutic solution to a target area within the intrathecal cavity.

The system may further comprise a sensor configured to determine the spatial orientation of the patient.

The sensor may be at least one of an accelerometer, a gyroscope or a magnetometer.

The sensor may comprise at least one of an accelerometer, a gyroscope or a magnetometer.

The system may further comprise an input element configured to enter the information regarding the spatial orientation of the patient to the processor.

The at least one catheter may further comprise a plurality of catheters, wherein each catheter of the plurality of catheters may be in fluid communication with at least one reservoir of the plurality of reservoirs.

Each catheter of the plurality of catheters may be encapsulated within a sheathing.

The plurality of catheters may be concentrically arranged.

A system implementation may comprise: at least a first catheter and a second catheter; at least a first reservoir and a second reservoir, wherein the first reservoir is in fluid communication with the at least first catheter and the second reservoir is in fluid communication with the second catheter; at least a first pump configured to control a rate of flow of fluid from the first reservoir through the at least first catheter; a second pump configured to control a rate of flow of fluid from the second reservoir through the second catheter; and a processor operably coupled with the at least first reservoir, the second reservoir, the at least first pump and the second pump, the processor configured to: determine a baricity of a therapeutic solution based on information regarding a baricity of fluids within each of the first reservoir and the second reservoir and a baricity of a solution within an intrathecal cavity, wherein the baricity of the solution is determined to be one of: hypobaric and hyperbaric based on an estimated location of a target area within the intrathecal cavity; provide instruction regarding an individual flow rate to the at least first pump and the second pump for distribution of fluids from the at least first reservoir and the second reservoir, based on the determined baricity; and provide instruction regarding a spatial orientation of the at least first catheter into the intrathecal cavity based on information regarding a spatial orientation of a person receiving the therapeutic solution and the determined baricity of the therapeutic solution.

The at least first catheter and the second catheter may be encased within a sheathing.

The at least first catheter may be concentrically arranged within the second catheter.

The system may further comprise: at least one sensor operably coupled with the processor, the processor further configured to: determine the spatial orientation of a patient as a function of the information regarding the spatial orientation of the patient, wherein the information regarding the spatial orientation is sensor information and the at least one sensor comprises at least one of: an accelerometer, a gyroscope, a magnetometer, an altimeter or a barometric pressure sensor.

The system may comprise an input device configured to provide information regarding the spatial orientation of the person to the processor, wherein the system may further comprise at least one inertial measurement unit (IMU) operably coupled with the processor, the processor further configured to modulate operation of the at least first pump and the second pump to control flow of the solution to the at least first catheter and the second catheter, the modulation determined by the processor as a function of spatial orientation information received from the at least one IMU.

A method implementation may comprise: determining at least one characteristic for each of a plurality of first fluids and a second fluid; determining a relative position of a distribution point of the plurality of first fluids with respect to a target area; determining at least one characteristic of a solution comprising the plurality of first fluids; adjusting the at least one characteristic of the solution based on the relative position of the distribution point with respect to the target area; and directing the solution to flow from the distribution point toward the target area through a cavity retaining the second fluid, thereby creating a distributed solution.

The at least one characteristic of each of the plurality of first fluids and the second fluid may comprise at least one of: a density and a viscosity.

Each of the plurality of first fluids may be independently delivered to the distribution point.

Adjusting the at least one characteristic of the solution may comprise determining a direction of gravitational force on the solution.

The at least one characteristic of the distributed solution may be adjusted to be less than the at least one characteristic of the second fluid, when the distribution point is oriented gravitationally below the target area.

The at least one characteristic of the distributed solution may be adjusted to be greater than the at least one characteristic of the second fluid, when the distribution point is oriented gravitationally above the target area.

The at least one characteristic of the distributed solution may be adjusted to be less than the at least one characteristic of the second fluid, wherein the distributed solution is directed in a direction substantially opposite acceleration due to gravity.

The at least one characteristic of the distributed solution may be adjusted to be greater than the at least one characteristic of the second fluid, wherein the distributed solution is directed in a direction substantially in-line with acceleration due to gravity.

The solution may be formed internal to the cavity.

The second fluid may be a cerebrospinal fluid.

A flowrate of each of the plurality of first fluids may be adjusted to achieve at least one desired adjusted characteristic of the solution.

The method may further comprise: aspirating fluid from the cavity, mixing the aspirated fluid with an additional quantity of at least one of the plurality of first fluids to form a second solution; injecting the second solution into the cavity; and directing the second solution to flow from the distribution point to the target area.

The method may further comprise: determining a relative timing for aspirating fluid from the cavity and injecting the second solution into the cavity, wherein the relative timing is determined as a function of a ratio of an injection flow rate of the second solution and an extraction flow rate of the aspirated fluid.

The cavity may be an intrathecal space and the second fluid is a cerebrospinal fluid.

A system implementation may comprise: a delivery system comprising: at least one port configured to receive a plurality of first fluids; and at least one lumen in fluid communication with the at least one port, the at least one lumen comprising at least one distribution orifice, wherein the at least one distribution orifice is configured to distribute the plurality of first fluids into an intrathecal space; and a control system comprising a plurality of reservoirs, each reservoir of the plurality of reservoirs containing a corresponding fluid of the plurality of first fluids; and a processor operably coupled with the control system and the delivery system, the processor configured to independently control individual flow of each of the plurality of first fluids from the plurality of reservoirs to the at least one port, wherein the at least one port is configured to distribute a solution comprising the plurality of first fluids to at least one lumen and the plurality of first fluids comprises a medication delivered to the intrathecal space.

The at least one lumen may comprise: a first lumen; and a second lumen comprising at least one distribution orifice, wherein each of the first lumen and the second lumen receive at least one fluid from the plurality of first fluids, wherein the received at least one fluid is distributed through at least one distribution orifice of at least one of the first lumen or the second lumen.

Each of first lumen and the second lumen may be encapsulated within a sheathing, wherein the sheathing comprises a plurality of sheathing distribution orifices.

The at least one lumen may comprise: a first lumen; and a second lumen comprising at least one distribution orifice, wherein the first lumen is contained within the second lumen, further wherein the first lumen and the second lumen receive at least one fluid from the plurality of first fluids, and wherein the solution is formed within the second lumen prior to distribution through the at least one distribution orifice.

The processor may be configured to independently control individual flow of each of the plurality of first fluids from the plurality of reservoirs to the at least one port based on a baricity of the solution, a barbotage of the solution, a spatial orientation of the at least one lumen, or a position of the at least one lumen relative to a target area within the intrathecal space.

The baricity of the solution may be based on at least one characteristic of at least one fluid within the intrathecal space.

The baricity of the solution may be less than a density of the at least one fluid within the intrathecal space when the target area is gravitationally above the at least one distribution orifice.

The baricity of the solution may be less than a density of the at least one fluid within the intrathecal space when the target area is gravitationally below the at least one distribution orifice.

The system may further comprise at least one bidirectional pump, wherein the processor may be configured to control the at least one bidirectional pump to aspirate fluid from the intrathecal space through the at least one port.

Apparatus and associated methods disclosed herein relate to fluidly coupling a plurality of lumens with a respective plurality of reservoirs, individually controlling release of a respective plurality of liquids from the plurality of reservoirs through the plurality of lumens and adjusting the baricity of a therapeutic mixture of the plurality of liquids. The plurality of lumens may be configured to be in fluid communication with a patient's intrathecal space. The plurality of lumens may be configured as separate catheters or a multiple-lumen catheter. The plurality of liquids may be a respective plurality of medication formulations. The plurality of medication formulations may have differing densities relative to cerebrospinal fluid (CSF). Formulation baricity may be adjusted by adding an excipient. Release of the plurality of liquids may be controlled by a respective plurality of pumps in fluid communication with the plurality of reservoirs. The adjusted therapeutic mixture baricity may be hypobaric, isobaric or hyperbaric relative to CSF.

Apparatus and associated methods disclosed herein relate to configuring a lumen first end to be in fluid communication with a patient's intrathecal space, fluidly coupling a lumen second end with a reservoir through a bidirectional pump, and alternating injection of liquid delivered from the reservoir through the lumen into the patient's intrathecal space with aspirating liquid from the patient's intrathecal space into the reservoir to agitate the delivered liquid, based on cycling bidirectional pump activation in alternating injection and aspiration directions. The liquid may comprise a medication. The aspirated liquid may comprise an admixture of the delivered medication and a portion of the patient's cerebrospinal fluid (CSF). The lumen may be a plurality of lumens. The plurality of lumens may have a respective plurality of lumen first ends in fluid communication with the patient's intrathecal space. The plurality of lumens may be configured as separate catheters or a multiple-lumen catheter.

Apparatus and associated methods disclosed herein relate to receiving sensor information indicating whether body orientation of a patient is supine or upright, adjusting baricity of a therapeutic mixture of a plurality of liquids as a function of the body orientation, based on individually controlling release of the plurality of liquids from a respective plurality of reservoirs through a plurality of lumens in fluid communication with a patient's intrathecal space, and in response to determining the body orientation changes to an updated body orientation, adjusting the baricity of the therapeutic mixture delivered to the intrathecal space as a function of the updated body orientation. The plurality of lumens may be configured as separate catheters or a multiple-lumen catheter. Therapeutic mixture delivery may be controlled by a respective plurality of pumps in fluid communication with the plurality of reservoirs. The therapeutic mixture baricity may be hypobaric, isobaric or hyperbaric relative to CSF.

In an aspect, a method is disclosed that provides for the timely distribution of a desired fluid (e.g., a medication) to a target area by the determination of characteristics of a solution containing the medication.

In an aspect, a system is disclosed that allows for the independent delivery of at least two fluids, at least one of which is a medication, into the intrathecal space via a double lumen catheter. The delivery of the medication may be programmatically controlled and dependent on device spatial orientation relative to the earth's gravitational field.

In an aspect, a system is disclosed for providing a formulation comprising at least two fluids, at least one fluid being a medication, wherein at least one fluid is capable of increasing or decreasing at least one characteristic (i.e., a density, specific gravity and/or viscosity) of the solution formed by the mixture of the at least two fluids.

In an aspect, a system is disclosed for providing the delivery of a plurality of fluids, at least one of which being a medication, is disclosed wherein the fluids are provided independently to a target area.

In an aspect, a system is disclosed for providing the delivery of a plurality of fluids, at least one fluid being a medication, which are mixed together prior for delivery to a target area.

In an aspect, a system is disclosed for providing delivery of at least one medication to a target area includes a processor that controls at least one of: a time, a duration and a quantity of fluids to be delivered to the target area.

In an aspect, a system is disclosed for determining a position of a fluid distribution point to a target, wherein the delivery of a solution of at least two fluids to the target is optimized by adjusting characteristics of the solution to flow rapidly through a fluid surrounding the target, wherein factors such as baricity, barbotage, distribution device orientation and relative position are considered.

In an aspect, a method is disclosed for programming a processor for determining a timing, a duration and a quantity of fluids to be delivered to the target area.

In accordance with the disclosed principles, while the delivery of specific medications is referred to, it would be understood by those skilled in the art that the systems and methods disclosed, herein, may be utilized to provide for a plurality of fluids to one or more target areas, wherein the fluids may not be related to the medical field.

Although the invention has been described with regard to a dual-fluid delivery system, it would be understood and recognized that the principles of the invention disclosed, herein, are also applicable to a system for a multi-fluid delivery system, without altering the scope of the invention claimed.

In addition, while the invention disclosed herein has been described with regard to the control, distribution and management of medication, such as morphine, delivered to an intrathecal cavity for the suppression of pain, it would be recognized that the invention disclosed is also applicable to other situations wherein the characteristics of a surrounding fluid and fluids, orientation, relative position, are applicable without altering the scope of the invention claimed.

The invention has been described with reference to specific embodiments. One of ordinary skill in the art, however, would appreciate and recognize that various modifications and changes can be made without departing from the scope of the invention as set forth in the claims.

Accordingly, the specification is to be regarded in an illustrative manner, rather than with a restrictive view, and all such modifications are intended to be included within the scope of the invention.

Each of the foregoing implementations can be employed individually or in conjunction.

Reference is made herein to particular features of various implementations. It is to be understood that the disclosure of particular features of various implementations in this specification is to be interpreted as including all possible combinations of such particular features. For example, where a particular feature is disclosed in the context of a particular aspect or implementation, or a particular claim, that feature can also be used—to the extent possible—in combination with and/or in the context of other particular aspects and implementations, and in an implementation generally.

While various implementations have been disclosed and described in detail herein, it will be apparent to those skilled in the art that various changes may be made to the disclosed configuration, operation, and form without departing from the spirit and scope thereof. In particular, it is noted that the respective implementation features, even those disclosed solely in combination with other implementation features, may be combined in any configuration excepting those readily apparent to the person skilled in the art as nonsensical. Likewise, use of the singular and plural is solely for the sake of illustration and is not to be interpreted as limiting.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

Therefore, it is intended that the invention not be limited to the particular embodiments disclosed as the best mode contemplated for carrying out this invention, but that the invention will include all embodiments falling within the scope of the present application as set forth in the following claims, wherein reference to an element in the singular, such as by use of the article "a" or "an" is not intended to mean "one and only one" unless specifically so stated, but rather "one or more."

Suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, chemical and thermal interaction. Two components may be functionally coupled to each other even though they are not in direct contact with each other. The terms "abutting" or "in mechanical union" refer to items that are in direct physical contact with each other, although the items may not necessarily be attached together. A first computing device configured to send an electronic message to a second computing device may send the electronic message through one or more other intervening systems. A first computing device configured to receive an electronic message from a second computing device may receive the electronic message through one or more other intervening systems.

One of ordinary skill in the art would appreciate that an exemplary system appropriate for use with implementation in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with implementations of the present disclosure include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and implementation of the present disclosure are contemplated for use with any computing device.

In the present disclosure "electronic message" should be understood to mean any form of electronic communication including but not limited to data packets, interrupts, button presses, function calls, error messages, visual indications, and the like.

As used herein, a singular term may include multiple objects. As used herein, a single element may include multiple such elements. For example, the term "computer" may include a single computer or multiple computers. The phrase "a computer that stores data and runs software," may include a single computer that both stores data and runs software, a first computer that stores data and a second computer that runs software, or multiple computers that together store data and run software, where at least one of the multiple computers stores data and at least one of the multiple computers runs software. For example, the term "processor" may include a single processor or multiple processors. The phrase "a processor that stores data and runs software," may include a single processor that both stores data and runs software, a first processor that stores data and a second processor that runs software, or multiple processors that together store data and run software, where at least one of the multiple processors stores data and at least one of the multiple processors runs software. An implementation comprising multiple processors may configure each particular processor of the multiple processors to exclusively execute only a particular task assigned to that particular processor. An implementation comprising multiple processors may configure each particular processor of the multiple processors to execute any task of multiple tasks assigned to that particular processor by a scheduler such that a different task may be assigned to different processors at different times. As used herein in an apparatus or a computer-readable medium, "at least one" object rather than or in addition to a single object may perform the claimed operations. For example, "a computer-readable medium" may be construed as "at least one computer-readable medium," and "an apparatus comprising a processor and a memory" may be construed as "a system comprising processing circuitry and a memory subsystem," or "a system comprising processing circuitry and memory" (where memory lacks the article 'a'). It should be noted that a skilled person would understand that "processing circuitry" may include a single processor or multiple processors. Similarly, "memory subsystem" or "memory" (lacking an article) may include a single memory unit or multiple memory unit.

In the present disclosure "digital indication" should be understood as synonymous and interchangeable with "electronic message."

In the Summary above, in this Detailed Description, the Claims below, the content of each of the applications incorporated by reference herein and in the accompanying drawings, reference is made to features of various embodiments of the invention. It is to be understood that the disclosure of embodiments of the invention in this specification includes all possible combinations of such features. For example, where a particular feature is disclosed in the context of a particular aspect or embodiment of the invention, or a particular claim, that feature can also be used—to the extent possible—in combination with and/or in the context of other aspects and embodiments of the invention, and in the invention generally.

Benefits, other advantages, and solutions to problems have been described above regarding specific embodiments. The benefits, advantages, and solutions to problems, and any element(s) that may cause any benefits, advantages, or solutions to occur or become more pronounced, are not to be construed as a critical, required, or an essential feature or element of any or all of the claims.

What is claimed is:

1. A method comprising:

implanting in a patient in need thereof a distribution system comprising an infusion port in fluid communication with at least one catheter comprising one or more catheter openings, wherein the at least one catheter is positioned to direct fluids within a cavity comprising a target area;

determining at least one characteristic comprising at least one of a density and a viscosity of each of a plurality of first fluids comprising a medication from at least one of an opioid pain medication, morphine, an anti-viral medication, an anti-bacterial medication, an anesthetic, Tetracaine, Novocain, Baclofen, saline and dextrose;

determining at least one characteristic comprising at least one of a density and a viscosity of a second fluid located within the cavity, said second fluid comprising a cerebrospinal fluid;

determining at least one characteristic comprising at least one of a density and a viscosity of a solution comprising the plurality of first fluids;

adjusting the at least one characteristic of the solution as required to direct the solution to the target area based on the at least one characteristic comprising the at least one of the density and the viscosity of the second fluid and a location of the implanted distribution system relative to the target area within the cavity;

delivering the solution to the cavity using the distribution system, thereby creating a distributed solution within the cavity;

aspirating the distributed solution from the cavity;

mixing the aspirated distributed solution from the cavity with an additional quantity of at least one of the plurality of first fluids to form a second solution within an internal patient reservoir; said second solution having the at least one characteristic required to direct the second solution to the target area within the cavity; and delivering the second solution from the internal patient reservoir into the cavity using the distribution system, thereby creating a second distributed solution.

2. The method according to claim 1, wherein each of the plurality of first fluids is independently delivered to a distribution point.

3. The method according to claim 1, wherein the adjusting the at least one characteristic of the solution comprises determining a direction of gravitational force on the solution.

4. The method according to claim 1, wherein at least one desired characteristic of the distributed solution is adjusted to be less than the at least one characteristic of the second fluid, when distribution point is oriented gravitationally below the target area.

5. The method according to claim 1, wherein at least one desired characteristic of the distributed solution is adjusted to be greater than the at least one characteristic of the second fluid, when a distribution point is oriented gravitationally above the target area.

6. The method according to claim 1, wherein at least one desired characteristic of the distributed solution is adjusted to be less than the at least one characteristic of the second fluid, wherein the distributed solution is directed in a direction substantially opposite acceleration due to gravity.

7. The method according to claim 1, wherein at least one desired characteristic of the distributed solution is adjusted to be greater than the at least one characteristic of the second fluid, wherein the distributed solution is directed in a direction substantially in-line with acceleration due to gravity.

8. The method according to claim 1, wherein a flowrate of each of the plurality of first fluids is adjusted to achieve at least one desired adjusted characteristic of the solution.

9. The method of claim 1, further comprising:

determining a relative timing for the aspirating the distributed solution from the cavity and the delivering the second solution from the internal patient reservoir into the cavity, wherein the relative timing is determined as a function of a ratio of an injection flow rate of the second solution and an extraction flow rate of the aspirated distributed solution.

* * * * *